US009844580B2

(12) United States Patent
Pilon-Clayton

(10) Patent No.: US 9,844,580 B2
(45) Date of Patent: Dec. 19, 2017

(54) RECOMBINANT HUMAN CC10 AND COMPOSITIONS THEREOF FOR USE IN THE TREATMENT OF NASAL RHINITIS

(71) Applicant: Therabron Therapeutics, Inc., Rockville, MD (US)

(72) Inventor: Aprile L. Pilon-Clayton, Germantown, MD (US)

(73) Assignee: Therabron Therapeutics, Inc., Rockville, MD (US)

( * ) Notice: Subject to any disclaimer, the term of this patent is extended or adjusted under 35 U.S.C. 154(b) by 0 days.

(21) Appl. No.: 15/042,790

(22) Filed: Feb. 12, 2016

(65) Prior Publication Data

US 2016/0158315 A1    Jun. 9, 2016

Related U.S. Application Data

(63) Continuation of application No. 12/945,622, filed on Nov. 12, 2010, now abandoned, which is a continuation of application No. PCT/US2009/043613, filed on May 12, 2009.

(60) Provisional application No. 61/052,861, filed on May 13, 2008.

(51) Int. Cl.
| | |
|---|---|
| A61K 38/17 | (2006.01) |
| A61K 9/10 | (2006.01) |
| A61K 9/00 | (2006.01) |
| A61K 45/06 | (2006.01) |
| A61K 47/02 | (2006.01) |
| A61K 47/10 | (2017.01) |
| A61K 47/18 | (2017.01) |
| C07K 14/435 | (2006.01) |
| C07K 14/47 | (2006.01) |

(52) U.S. Cl.
CPC ........ *A61K 38/1709* (2013.01); *A61K 9/0043* (2013.01); *A61K 45/06* (2013.01); *A61K 47/02* (2013.01); *A61K 47/10* (2013.01); *A61K 47/186* (2013.01); *C07K 14/435* (2013.01); *C07K 14/47* (2013.01)

(58) Field of Classification Search
CPC .... A61K 38/1709; A61K 38/00; A61K 38/17; C07K 14/47; C07K 14/00
See application file for complete search history.

(56) References Cited

U.S. PATENT DOCUMENTS

| | | | |
|---|---|---|---|
| 4,691,009 A | 9/1987 | Palmer | |
| 4,820,514 A | 4/1989 | Cummins | |
| 4,917,826 A | 4/1990 | Johnson | |
| 5,266,562 A | 11/1993 | Mukherjee | |
| 5,354,269 A | 10/1994 | Goodheart | |
| 5,470,885 A | 11/1995 | Fuhrman | |
| 5,482,930 A | 1/1996 | Wei | |
| 5,491,130 A | 2/1996 | Roberts | |
| 5,618,786 A | 4/1997 | Roosdorp | |
| 5,696,092 A | 12/1997 | Patierno | |
| 5,817,750 A | 10/1998 | Ruoslahti | |
| 6,066,724 A | 5/2000 | Ni | |
| 6,255,281 B1 | 7/2001 | Pilon | |
| 7,122,344 B2 | 10/2006 | Pilon | |
| 7,846,899 B2 | 12/2010 | Pilon | |
| 2002/0006640 A1 | 1/2002 | Ni | |
| 2002/0025510 A1 | 2/2002 | Strongin | |
| 2002/0160948 A1 | 10/2002 | Pilon | |
| 2002/0169108 A1 | 11/2002 | Pilon | |
| 2002/0173460 A1 | 11/2002 | Pilon | |
| 2003/0008816 A1 | 1/2003 | Pilon | |
| 2003/0109429 A1 | 6/2003 | Pilon | |
| 2003/0207795 A1 | 11/2003 | Pilon | |
| 2004/0047857 A1 | 3/2004 | Pilon | |
| 2005/0026139 A1 | 2/2005 | Fang | |
| 2005/0261180 A1 | 11/2005 | Pilon | |
| 2006/0025348 A1 | 2/2006 | Pilon | |
| 2006/0281681 A1 | 12/2006 | Pilon | |
| 2008/0064633 A1 | 3/2008 | Pilon | |
| 2009/0029917 A1 | 1/2009 | Pilon | |
| 2009/0197808 A1 | 8/2009 | Pilon | |
| 2009/0227025 A1 | 9/2009 | Nichols | |
| 2009/0253174 A1 | 10/2009 | Serber | |

(Continued)

FOREIGN PATENT DOCUMENTS

| | | |
|---|---|---|
| WO | 9608572 | 3/1996 |
| WO | 9640657 | 12/1996 |

(Continued)

OTHER PUBLICATIONS

Liu et al. The expression of osteopontin and its associated with Clara cell 10 kDa protein in allergic rhinitis. Clin Exp Allergy 40: 1632-1641, 2010.*
Long et al. Clara cell 10-kDa protein gene transfection inhibits NF-KB activity in airway epithelial cells. PLoS One 7(4): e35960, 2012. (9 pages).*
Wang et al. Clara cell 10-kd protein suppress chitinase 3-like 1 expression associated with eosinophilic chronic rhinosinusitis. Am J Respir Crit Care Med 181: 908-916, 2010.*
Wang et al. Clara cell 10-kd protein in inflammatory upper airway diseases. Curr Opin Allergy Clin Immunol 13: 25-30, 2013.*

(Continued)

*Primary Examiner* — Bridget E Bunner
(74) *Attorney, Agent, or Firm* — Henry J. Cittone; Cittone & Chinta LLP

(57) ABSTRACT

The present invention relates generally to the use of recombinant human CC10 (rhCC10), also known as recombinant human uteroglobin, for use as a therapeutic in the treatment of nasal rhinitis, nasal sinusitis, chronic rhinosinusitis, and nasal polyposis. More particularly, the invention provides methods, including broadly the critical dosage ranges of rhCC10 and intranasal route of administration, which may be administered to safely and effectively treat the aforementioned conditions. The invention further provides a composition useful in administering rhCC10 to humans.

45 Claims, No Drawings

(56) References Cited

U.S. PATENT DOCUMENTS

| | | |
|---|---|---|
| 2010/0183640 A1 | 7/2010 | Pilon |
| 2011/0183887 A1 | 7/2011 | Pilon |
| 2011/0240012 A1 | 10/2011 | Pilon |
| 2012/0231997 A1 | 9/2012 | Pilon |

FOREIGN PATENT DOCUMENTS

| | | |
|---|---|---|
| WO | 9701627 | 1/1997 |
| WO | 9853846 | 12/1998 |
| WO | 9952493 | 10/1999 |
| WO | 0072868 | 12/2000 |
| WO | 0179285 | 10/2001 |
| WO | 03003979 | 1/2003 |
| WO | 03057257 A1 | 7/2003 |
| WO | 2007109118 | 9/2007 |
| WO | 2009140269 | 11/2009 |
| WO | 2011047065 | 4/2011 |

OTHER PUBLICATIONS

Ray, "Cloning and Characterization of the Mouse Clara Cell Specific 10 kDa Protein Gene Comparison of the 5'-Flanking Region With the Human Rat and Rabbit Gene", Biochemical and Biophysical Research Communications 197 (1):11:163-171 (Nov. 1993).

Rennard, "Production of Fibronectin by the Human Alveolar Macrophase: Mechanism for the Recruitment of Fibroblasts to Sites of Tissue Injury in Interstitial Lung Diseases" Proceedings of the National Academy of Sciences USA, 78(11):7147-7151 (Nov. 1981).

Ricci, "Common Structural Stability Properties of 4-Helicle Bundle Cykotines: Possible Physiological and Pharmaceutical Consequences." Current Pharmacy Design 10(31): 3901-3911 (Jan. 2004).

Robinson, D., "Macromolecular Transport in Rabbit Blastocysts: Evidence for a Specific Uteroglobin Transport System." Molecular and Cellular Endocrinology 63(1-2): 227-237 (May 1989).

Ruoslahti, "Fibronectin and Its Receptors." Annual Review of Biochemistry 57:374-413 (Jan. 1988).

Scheuer, W., "Phospholipase A2-regulation and inhibition." Klin Wochenschr 67:153-159 (Feb. 1989).

Shijubo, N., "Serum and BAL Clara Cell 10 kDa Protein (CC10) Levels and CC10-Positive Bronchiolar Cells Are Decreased in Smokers." European Respiratory Journal 10(5):1108-1114 (May 1997).

Shimizu, "Establishment of a Standardized Assay System of Fibronectin Activity Using Flbronectin-Medicated Cell Adhesion." Biological and Pharmaceutical Bulletin 20(12):1219-1223 (Dec. 1997).

Shin, "Enhanced Production of Human Mini-Proinsulin in Fed-Batch Cultures at High Cell Density of *Esherichia coli* BL21(DE3)(pET-3aT2M2]." Biotechnology Progress 13(3):249-257 (May 1997).

Singh, "Identification, Cellular Localization, Isolation, and Characterization of Human Clara Cell-Specific 10 KD Protein." Journal of Histochemistry and Cytochemistry 36(1):73-80 (Jan. 1988).

Singh, "Mouse Clara Cell 10-kDa (CC10) Protein: cDNA Nucleotide Sequence and Molecular Basis for the Variation of Progesterone Binding of CC10 from Different Species." Experimental Lung Research 19(1): 67-75 (Jan. 1993).

Singh, "Isolation and Amino Acid Composition of the Isotypes of a Rat Clara Cell Specific Protein." Experimental Lung Research 13(3):299-309 (Jan. 1987).

Sipes, "Inhibition of Fibronectin Binding and Flbronectin-Medication Cell Adhesion to Collagen by a Peptide by the Second Type I Repeat of Thrombospodin." Journal of Cell Biology 121(2):469-477 (Apr. 1993).

Steward, "Sequence Conservation in IG-Like Domains: the Role of Highly Conserved Proline Residues in the Fibronectin Type III Superfamily." Journal of Molecular Biology 318(4):935-940 (May 2002).

Stripp, "Clara cell secretory protein: a determinant of PCB bioaccumulation in mammals." American Journal of Physiology 274(4 part 1):L656-L664 (Oct. 1996).

Stripp, "Plasticity of airway cell proliferation and gene expression after acute naphthalene injury." American Journal of Physiology 269(6 part 1):L791-L799 (Dec. 1995).

Stripp, "Structure and Regulation of the Murine Clara Cell Secretory Protein Gene." Genomics 20(1):27-35 (Mar. 1994).

Stripp, "cis-Acting Elements That Confer Lung Epithelial Cell Expression of the CC.sub.10 Gene." Journal of Biological Chemistry 267(21):14703-14712 (Jan. 1992).

Torkkeli, "Uterine and lung uteroglobins in the rabbit. Two similar proteins with differential hormonal regulation." Biochemica et Biophysica Acta 544(3):578-592 (Dec. 1978).

Tykka, "A randomized double-blind study using CaNa2EDTA, a phospholipase A2 inhibitor, in the management of human acute pancreatitis." Scand Journal of Gastroenterology 20(1):5-12 (Jan. 1985).

Tykka, "Phospholipase A2 inhibitors and their possible clinical use in the treatment of acute pancreatitis." Scand J Gastroenterology 15(5):519-28, Abstract only (Jan. 1980).

Umland, "Structure of human Clara cell phopholipid-binding protein-ligand complex at 1.9 A resolution." Nature Struct. Biol. 1:538-545 (Jan. 1994).

Umland, "Twixt form and function," Nat. Struct. Biol. 2(11):919-922 (Nov. 1995).

UniProt Accession No. P10145 (IL8_Human. Jul. 1, 1989).

Vadas, "Potential therapeutic efficacy of inhibitors of.,.," Agents Actions 19(3-4):94-202 (Nov. 1986).

Van Bisbergen, "Synthetic peptide from lipocortin 1 has no phospholipase inhibitory activity." FEBS Letters 247:293-297 (Jan. 1989).

Van Winkle L., "Repair of Naphthalene-Injured Microdissected Airways in vitro." American Journal of Respiratory Sell and Molecular Biology 15(1): 1-8 (Jul. 1996).

Vostal, J.,"Novel Peptides Derived From a Region of Local Homology Between Uteroglobin and Lipocortin-1 Inhibit Platelet Aggregation and Secretion." Biochemical and Biophysical Research Communications 165(1): 27-36 (Nov. 1989).

Watts, "Effect of Dexamethasone Therapy on Fibronectin and Albumin Levels in Lung Secretions of Infants with Bronchopulmonaw Dysplasia." Journal of Pediatrics 121(4): 597-607 (Oct. 1992).

Wolf, "Human CC10, the homologue of rabbit uteroglobin: genomic cloning, chromosomal localization and expression in endometrial cell lines." Hum MOI Genet 1(6):371-378 (Sep. 1992).

Wu, C., "Integrin Activation and Cytoskeletal Interaction Are Essential for the Assembly of a Fibronectin Matrix." Cell 83(5): 715-724 (Dec. 1995).

Wuenschell, C., "Embryonic Mouse Lung Epithelial Progenitor Cells Co-Express Immunohistochemical Markers of Diverse Mature Cell Lineages." The Journal of Histochemistry and Cytochemistry 44(2): 113-123 (Jan. 1996).

Zhang, "Modulation of Cell Surface Fibronectin Asembly Sites by Lysophosphatidic Acid." Journal of Cellular Biology 127(5):1447-1459 (Dec. 1994).

Zhang, "Cross-linking of the NH.sub.2-Terminal Region of Fibronectin to Molecules of Large Apparent Molecular Mass." The Journal of Biological Chemistry 271(52): 33284-33292 (Jan. 1996).

Nord M., "Decreased serum and bronchoalveolar lavage levels of Clara cell secretory protein (CC16) is associated with bronchiolitis obliterans syndrome and airway neutrophilia in lung transplant recipients." Transplantation. 73 (8):1264-9 (Apr. 2002).

Ramsay PL, "Clara cell secretory protein oxidation and expression in premature infants who develop bronchopulmonary dysplasia." American Journal of Respiratory Critical Care Medicine 164(1):155-61 (Jul. 2001).

Geerts L., "Natural inhibitors of neutrophil function in acute respiratory distress syndrome." Critical Care Medicine 29 (10):1920-4 (Oct. 2001).

(56) References Cited

OTHER PUBLICATIONS

Wang SZ, "CCSP modulates airway dysfunction and host responses in an Ova-challenged mouse model." American Journal of Physiology Lung Cellular and Molecular Physiology 281(5):L1303-11 (Nov. 2001).

Miller TL, "Recombinant human Clara cell secretory protein in acute lung injury of the rabbit: effect of route of administration." Pediatric Critical Care Medicine 6(6):698-706 (Nov. 2005).

Miller TL, "Effects of an intratracheally delivered anti-inflammatory protein (rhCC10) on physiological and lung structural indices in a juvenile model of acute lung injury." Biology of the Neonate 89(3):159-70 (Jan. 2006).

Shashikant BN, "Dose response to rhCC10-augmented surfactant therapy in a lamb model of infant respiratory distress syndrome: physiological, inflammatory, and kinetic profiles." Journal of Applied Physiology 99(6):2204-11. (Dec. 2005) Epub Aug. 4, 2005.

Mandal AK, "Uteroglobin inhibits prostaglandin F2alpha receptor-mediated expression of genes critical for the production of pro-inflammatory lipid mediators." Journal of Biological Chemistry 280(38):32897-904. (Sep. 2005) Epub Aug. 1, 2005.

Mattsson J, "Decreased serum levels of clara cell secretory protein (CC16) are associated with bronchiolitis obliterans and may permit early diagnosis in patients after allogeneic stem-cell transplantation." Transplantation79 (10):1411-6 (May 2005).

Welty SE, "CC10 administration to premature infants: in search of the "silver bullet" to prevent lung inflammation." Pediatric Resources 58(1):7-9. (Jul. 2005) Epub May 5, 2005.

Benson M., "Gene profiling reveals decreased expression of uteroglobin and other anti-inflammatory genes in nasal fluid cells from patients with intermittent allergic rhinitis." Clinical and Experimental Allergy 35(4):473-8 (Apr. 2005).

Johansson S., "Low levels of CC16 in nasal fluid of children with birch pollen-induced rhinitis." Allergy 60(5):638-42 (May 2005).

Levine CR, "The safety, pharmacokinetics, and anti-inflammatory effects of intratracheal recombinant human Clara cell protein in premature infants with respiratory distress syndrome." Pediatric Resources 58(1):15-21 (Jul. 2005) Epub Mar. 17, 2005.

Ray R, "Uteroglobin suppresses SCCA gene expression associated with allergic asthma." Journal of Bilogical Chemistry 280(11):9761-4. (Mar. 2005) Epub Jan. 27, 2005.

Yoshikawa S, "Clara cell secretory protein and phospholipase A2 activity modulate acute ventilator-induced lung Injury in mice." Journal of Applied Physiology 98(4):1264-71. (Apr. 2005) Epub Dec. 17, 2004.

Ye Q, "Serum CC-10 in inflammatory lung diseases." Respiration. 71(5):505-10 (Sep. 2004).

Hung CH, "Regulation of TH2 responses by the pulmonary Clara cell secretory 10-kd protein." Journal of Allergy and Clinical Immunology 114(3):664-70 (Sep. 2004).

Mandal AK, "Uteroglobin represses allergen-induced inflammatory response by blocking PGD2 receptor-mediated functions." Journal of Experimental Medicine 199(10):1317-30 (May 2004).

Iannuzzi MC. "Clara cell protein in sarcoidosis: another job for the respiratory tract protector?" American Journal of Respiratory Critical Care Medicine 169(2):143-4 (Jan. 2004).

Nosratabadi AR, "Clara cell 10-KDA protein inhibits endotoxin-induced airway contraction in isolated perfused rat lungs." Experimental Lung Research 29(7):455-73 (Oct. 2003).

Ramsay PL, "Multiple mechanisms for oxygen-induced regulation of the Clara cell secretory protein gene." FASEB Journal 17(14):2142-4. (Nov. 2003) Epub Sep. 18, 2003.

Wang SZ, "Clara cell secretory protein modulates lung inflammatory and immune responses to respiratory syncytial virus infection." Journal of Immunology 171(2):1051-60 (Jul. 2003).

Chandra S., "Safety and efficacy of intratracheal recombinant human Clara cell protein in a newborn piglet model of acute lung injury." Pediatric Research 54(4):509-15. (Oct. 2003) Epub Jun. 18, 2003.

Shijubo N., "Clinical aspects of Clara cell 10-kDa protein/uteroglobin (secretoglobin 1A1)." Current Pharmaceutical Design 9(14):1139-49 (Jan. 2003).

Angert, "CC10 reduces inflammation in meconium aspiration syndrome in newborn piglets." Pediatric Research 62 (6):684-688 (Dec. 2007).

Yoshikawa S. "Clara cell secretory protein and phospholipase A2 activity modulate acute ventilator-induced lung injury in mice." Journal of Applied Physiology 98(4):1264-71 (Apr. 2005).

Castro, "Attenuation of Pulmonary Neuroendocrine Differentiation in Mice Lacking Clara Cell Secretory Protein" Laboratory Investigation 80,(10):1533 (Oct. 2000).

Kim, "IL-13-induced Clara cell secretory protein expression in airway epithelium: role of EGFR signaling pathway." American Journal of Physiology Lung Cellular and Molecular Physiology 283:67-75 (Feb. 2002).

Liu, "Gene expression profiles in human nasal polyp tissues studied by means of DNA microarray." Journal of Allergy and Clinical Immunology 114(10): 783-790 (Oct. 2004).

Magdaleno, "Interferon-gamma regulation of Clara cell gene expression: in vivo and in vitro." American Physiological Society 272(6 Pt 1):L1142-L1151 (Jun. 1997).

Ikegami M., "CCSP deficiency does not alter surfactant homeostasis during adenoviral infection." American Journal of Physiology 277(5 Pt 1):L983-7 (Nov. 1999).

Hendrickson, "Development of Lentiviral Vectors with Regulated Respiratory Epithelial Expression In Vivo." American Journal or Respiratory Cell and Molecular Biology 37(4); 414-423, Tables 1&2 (Jun. 2007).

Murakami, "Mini-plasmin found in the epithelial cells of bronchioles triggers infection by broad spectrum influenza A viruses and Sendai virus." European Journal of Biochemistry 268:2847-2855; p. 2853, col. 2, pra 1 tp p. 2854 col. 1 para 3 (May 2001).
Endo, "Growth of Influence a Virus in Primary, Differentiated Epithelial Cells Derived from Adenoids." Journal of Virology 70(3):2055-2058; p. 2057 (Mar. 1996).
Islam, "Acquisition of Pathogenicity of a Newcastle Disease Virus Isolated from a Japanese Quail by Intracerebral Passage in Chickens." Japanese Journal of Veterinary Research 42(3-4):147-156; Abstract, Tables 3-5 (Jan. 1995).
Widegren, "Effects of Clara cell 10 (CC10) protein on symptoms and signs of allergic rhinitis." Annals of Allergy Asthma and Immunology 102(1):51-6 (Jan. 2009).
Liu, "Clara cell 10-kDa protein expression in chronic rhinosinusitis and its cytokine-driven regulation in sinonasal mucosa." Allergy 64(1):149-57. (Jan. 2009) Epub Dec. 12, 2008.
Benson, "Inverse relation between nasal fluid Clara Cell Protein 16 levels and symptoms and signs of rhinitis in allergen-challenged patients with intermittent allergic rhinitis. "Allergy 67(2):178-83. (Feb. 2007).
Fritz, "Nasal mucosal gene expression in patients with allergic rhinitis with and without nasal polyps." Journal of Allergy and Clinical Immunology 12(6):1057-63 (Dec. 2003).
Liu, "CC10 Expression and Its Cytokine-driven Regulation in Chronic Rhinosinusitis." Journal of Allergy and Clinical Immunology 121(2):Suppl. 1:S72 (Feb. 2008).
Pilon, AL, "The Development of Recombinant Human Uteroglobin/CC10 as a Therapeutic Agent in Inflammatory and Fibrotic Disease". Annals of the New York Academy of Sciences. vol. 293, pp. 280-299 (Dec. 2000).
Farrow, J., "Binding of rhCC10 to Fibronectin and Its Effect on Cellular Adhesion." Annals of the New York Academy of Sciences. vol. 293, pp. 338-342 (Dec. 2000).
Mukherjee A.B., "Uteroglobin: a novel cytokine?" Cellular and Molecular Life Sciences 55:771-787, (May 1999).
Matthews, J.H., "Crystallization and characterization of the recombinant human Clara cell 10-kDa protein." Proteins 20:191-196 (Oct. 1994).
Zhang, Z., "Human Uteroglobin Gene: Structure, Subchromosomal Localization, and Polymorphism." DNA & Cell Biol. 16:73-83 (May 1997).

(56) References Cited

OTHER PUBLICATIONS

Peri, A., "Tissue-specific expression of the gene coding for human Clara cell 10-kD protein, a phospholipase A2-Inhibitory protein." Journal of Clinical Investigations 92:2099-2109 (Nov. 1993).
Bernard, A., "Human urinary protein 1: Evidence for identity with the Clara cell protein and occurrence in respiratory tract and urogenital secretions." Clinical Chimica Acta 207:239-249 (May 1992).
Jackson, P.J., "Purification and Partial Amino Acid Sequence of Human Urine Protein 1: Evidence for Homology with Rabbit Uteroglobin." Journal of Chromatography 452:359-367 (Oct. 1988).
Levin, S.W., "Uteroglobin inhibits phospholipase A2 activity." Life Sciences 38:1813-1819 (May 1986).
Mantile, G., "Human Clara cell 10-kDa protein is the counterpart of rabbit uteroglobin." Journal of Biological Chemistry 268:20343-20351 (Sep. 1993).
Vasanthakumar, G., "Inhibition of phagocyte chemotaxis by potent phospholipase A2 inhibitory protein, Uteroglobin." Biochemical Pharmacology 37:389-394 (Jan. 1988).
Lesur, O. "Clara Cell Protein (CC-16) Induces a Phospholipase A2-mediated Inhibition of Fibroblast Migration In Vitro." American Journal Respiratory and Critical Care Medicine 152:290-297 (Jul. 1995).
Dierynck, I.A., "The human Clara cell protein: biochemical and biological characterization of a natural Immunosuppressor" Multiple Sclerosis 1:385-387 (Jan. 1996).
Leyton, J., "Recombinant human uteroglobin inhibits the in vitro invasiveness of human metastatic prostate tumor cells and the release of arachidonic acid stimulated by fibroblast-conditioned medium." Cancer Research, 54: 3696-3699 (Jul. 1994).
Zhang, Z., "Severe Fibronectin-Deposit Renal Glomerular Disease in Mice Lacking Uteroglobin" Science Magazine 276:1408-1412 (May 1997).
Miele, L., "Uteroglobin and uteroglobin-like proteins: the uteroglobin family of proteins." J Endocrinol Invest 17:679-692 (Sep. 1994).
Johnston, C.J., "Altered Pulmonary Response to Hyperoxia in Clara Cell Secretory Protein Deficient Mice." American Journal of Respiratory Cell and Molecular Biology 17:147-155 (Aug. 1997).
Mango, G.W., "Clara cell secretory protein deficiency increases oxidant stress response in conducting airways." American Journal of Physiology 275:L348-56 (Aug. 1998).
Harrod, KS., "Clara cell secretory protein decreases lung inflammation after acute virus infection." American Journal of Physiology 275:L924-30 (Nov. 1998).
Bernard, A.M., "Serum Clara cell protein: an indicator of bronchial cell dysfunction caused by tobacco smoking." Environmental Research 66:96-104 (Jul. 1994).
Bernard, A.M, "Clara cell protein in serum and bronchoalveolar lavage." European Respiratory Journal 5:1231-1238 (Jan. 1992).
Dhanireddy, R., T. "Detection of a rabbit uteroglobin-like protein in human neonatal tracheobronchial washings." Biochemical and Biophysical Research Communications 152:1447-1454 (May 1988).
Doyle, I.R., "Clearance of Clara Cell Secretory Protein 16 (CC16) and Surfactant Proteins A and B from Blood in Acute Respiratory Failure" American Journal of Respiratory Critical Care Medicine 158:1528-1535 (Nov. 1998).
Jorens, P., "Potential role of Clara cell protein, an endogenous phospholipase A2 inhibitor, in acute lung injury." European Respiratory Journal 8:1647-1653 (Oct. 1995).
Hermans, C., "Pneumoproteinaemia: a new perspective in the assessment of lung disorders." European Respiratory Journal 11:801-803 (May 1998).
Van Vyve, "Protein content in bronchoalveolar lavage fluid of patients with asthma and control subjects." Journal of Allergy and Clinical Immunology 95:60-68 (Jan. 1995).
Shijubo, "Serum Levels of Clara Cell 10-kDa Protein Are Decreased in Patients with Asthma." Lung 177:45-52 (Jan. 1999).

Nomori, H., "Protein 1 (Clara Cell Protein) Serum Levels in Healthy Subjects and Patients with Bacterial Pneumonia." American Journal of Respiratory Critical Care Medicine 152:746-750 (Aug. 1995).
Dhanireddy, R., "Uteroglobin-like Protein in Premature Infants: Effect of Gestational Age." Pediatric Research 23:463A (Jan. 1988).
Singh, G. "Clara Cells and Clara Cell 10 kDa Protein (CC10)." American Journal of Respiratory Cell and Molecular . Biology 17:141-143 (Jan. 1997).
Dhanireddy, R., "Uteroglobin-like protein levels in premature infants on long term ventilator support." Pediatric Research 33:323A (Jan. 1993).
Bernard, A., "Clara Cell Protein in Human Amniotic Fluid: A Potential Marker of Fetal Lung Growth." Pediatric Research 36:771-775 (Dec. 1994).
Lopez De Haro, M.S., "Binding of retinoids to uteroglobin." Federation of Biochemicals Society Letters 349:249-251 (Aug. 1994).
Singh, G., "Clara cell 10 kDa protein (CC10): comparison of structure and function to uteroglobin." Biochim Biophys Acta 1039:348-355 (Jul. 1990).
Peri, A., "Uteroglobin gene expression in the rabbit uterus throughout gestation and in the fetal lung: Relationship between uteroglobin and eicosanoid levels in the developing fetal lung." Journal of Clinical Investigation 96:343-353 (Jul. 1995).
Davis, J.M., "Chronic Lung Disease." In: Neonatology:pathophysiology and Management of the Newborn, edited by Avery, G.B., Fletcher, M.A. and MacDonald, M.G. p. 453-477 (Jan. 1994).
Whitsett, J.A., "Acute Respiratory Disorders." In: Neonatology:pathophysiology and Management of the Newborn, edited by Avery, G.B., Fletcher, M.A. and MacDonald, M.G. p. 429-452 (Jan. 1994).
Stenmark, K., "Potential Role of Eicosanoids and PAF in the Pathophysiology of Bronchopulmonary Dysplasia." American Review of Respiratory Diseases 136:770-772 (Jan. 1987).
Volovitz, B., "Relationship between leukotriene C4 and an uteroglobin-like protein in nasal and tracheobronchial mucosa of children. Implication in acute respiratory illnesses." International Archives of Allergy Applied Immunology 36:420-425 (Jan. 1988).
Hermans, C., "Clara cell protein as a marker of Clara cell damage and bronchoalveolar blood barrier permeability." European Respiratory Journal 13:1014-1021 (May 1999).
Lensmar, C., "Decreased pulmonary levels of the anti-inflammatory Clara cell 16 kDa protein after induction of airway inflammation in asthmatics." Cellular and Molecular Life Sciences 57:976-981 (Jun. 2000).
Lassus P., "Clara-cell secretory protein in preterm infants' tracheal aspirates correlates with maturity and increases in infection." Pediatric Pulmonology 30(6):466-9 (Dec. 2000).
Chen LC, "Cutting edge: altered pulmonary eosinophilic inflammation in mice deficient for Clara cell secretory 10-kDa protein." Journal of Immunology 167(6):3025-8 (Sep. 2001).
Diernyck, I., "Potent inhibition of both human interferon-gamma production and biologic activity by the Clara cell protein, CC16." American Journal of Respiratory Cell and Molecular Biology 12(2):205-10 (Feb. 1995).
Shijubo N, "Clara cell protein-positive epithelial cells are reduced in small airways of asthmatics." American journal of Respiratory and Critical Care Medicine 160(3):930-3 (Sep. 1999).
Khoor A., "Ontogeny of Clara cell-specific protein and its mRNA: their association with neuroepithelial bodies in human fetal lung and in bronchopulmonary dysplasia." Journal of Histochemistry and Cytochemistry 44(12):1429-38 (Dec. 1996).
Mukherjee, A.B., "Regulation of Extracellular Phospholipase A2 Activity: Implications for Inflammatory Diseases." DNA and Cell Biology 11:233-243 (Apr. 1992).
Abman "Pathophysiology and Treatment of Bronchopulmonary Dysplasia: Current Issues." Pediatric Clinics of North America 41(2):277-315 (Apr. 1994).
Akiyama "Fibronectin and Integrins in Invasion . . . " Cancer and Metastasis Reviews 14(3):173-189 (Sep. 1995).

(56) References Cited

OTHER PUBLICATIONS

Andersson, "Heterologous Expression of Human Uteroglobin/Polychlorinated Biphenyl-binding Protein." Journal of Biological Chemistry 269(29):19081-19087 (Jul. 1994).
Aoki, "Isolation of Human Uteroglobin from Blood Filtrate." Molecular Human Reproduction 2(7):489-497 (Jul. 1996).
Assmann, "Familial Glomerulonephritis Characterized by Massive . . . " American Journal of Kidney Diseases 25 (5):781-791 (May 1995).
Badcock, "False-Positive EMIT.RTM.-st.TM. Ethanol Screen with Post-Mortem Infant Plasma." Clinical Chemistry 38 (3):434-435 (Mar. 1992).
Bischoff, "Purification and Biochemical Characterization of Recombinant alpha1-antilrypsin variants expressed in E. coli." Biochemistry 30(14):3464-3472 (Apr. 1991).
Bowton, "Phospholipase A2 and arachidonate increase in bronchoalveolar lavage fluid after inhaled antigen challenge in asthmatics." American Journal of Respiratory Critical Care Medicine 155(2):421-5 (Feb. 1997).
Camussi, "Antiflammins Inhibit Synthesis of Platelet-Activating Factor and Intradermal Inflammatory Reactions." Advances in Experimental Medicine and Biology 1:171(3):913-27, Abstract (Mar. 1990).
Chan, "Effects of antiflammins on endotoxin-induced uveitis in rats" Archives of Ophtamology 1099(2):278-281 (Feb. 1991).
Chiesa, "Significant increase in immunoregulaton; protein blastokinin/uteroglobin in IgA/firbronectin complexes in sera of patients with IgA nephropathy." Nephrology Dialysis Transplantation 15(9):A39 (Jan. 2000).
Chilton, "Antigen-induced generation of lyso-phospholipids in human airways." Journal of Experimental Medicine 183(5): 2235-2245 (May 1996).
ClaraGen Inc. Press Release."Claragen Explores How Uteroglobin Can Prevent Neonatal Lung Disease." (Jun. 2, 1997).
Clement; Rev Mal Respir 13(3):243-9 (Jul. 1996).
Dennis E.A., "Potential phopholipase A2s involved in inflammatow diseases." Agents Actions Suppl. 46:3539, see p. 35, full para. 2. (Jan. 1995).
Edelson, "Acute lung injury induced by phospholipase A2: 2, 7 Structural and funcational changes." Am. Rev. Respir. Dis. 143:1102-1109, see p. 1102, col. 1, full paragraph 1, paragraphs bridging cols. 1-2 and cols. 2-3, paragraph bridging pp. 1105-1106 (May 1991).
Gonzalez, "Biding of uteroglobin to microsomes and plasmatic membranes." Federation of European Biochemical Societies Letters. 361(2-3): 225-258, see p. 257, Figure 4. (Mar. 1995).
UniProt Basic UniProtKB Entry Viewer, Uter_Human. Oct. 1, 1989, Accession No. P11684.
Guy J. et al. Surfactant-producing rabbit pulmonary alveolar type II cells synthesize and secrete an anti-inflammatory protein, uteroglobin. Biochemical and Biophysical Research Communications, vol. 189, No. 2, Dec. 15, 1992 (Dec. 15, 1995), pp. 662-669, XP002153573.
Information Hyperlinked Over Proteins—SCGB1A1—secretglobin, family 1A, member 1 (uteroglobin), Last accessed 44 Dec. 2007.
Jarjour, "Antigen-induced airway inflammation in atopic subjects generates dysfunction of pulmonary surfactant." American Journal Respiratory Critical Care Medicine 160(1)1336-41 (Jul. 1999).
Konstan, "Effect of high-dose ibuprofen in patients with cystic fibrosis." New England Journal of Medicine 332 (13):848-54 (Mar. 1995).
Kundu, "Recombinant human uteroglobin suppresses cellular invasiveness via a novel class of high-affinity cell surface binding site." Proceedings of the National Academy of Sciences U.S.A 93(7): 2915-2919, see p. 2915. para. bridging cols. 1-2. (Apr. 1996).
Lindhal, "Demonstration of different forms of lipocortin-1 and Clara cell protein-16 in human nasal and bronchoalveolar lavage fluids." Electrophoresis 20: 881-890 (Jan. 1999).

Liu, "Pulmonary surfactant given prophylactically alleviates an asthma attack in guinea-pigs." Clinical and Experimental Allergy 26(3):270-5 (Mar. 1996).
Lloret, "Effect of Nonapeptide Fragments of Uteroglobin and Lipocortin I on Oedema and Mast Cell Degranulation." European Journal of Pharmacology 264(3): 379-384 (Nov. 1994).
Toh, "Protein 1: Its Purification and Application in Clinical Medicine" Journal of Clinical Laboratory Analysis 7 (6):394-400 (Jan. 1993).
Lunardi-Iskander, Y., "Effects of A Urinary Factor from Women in Early Preganancy of HIV I, SID and associated Disease", Nature Medicine 4(4):428-434 (Sep. 1998).
Makrides, "Strategies for Achieving High-Level Expression of Genes in Escherichia coli." Microbiological Reviews, American Society for Microbiology, Washington DC, US 60(3) ISSN: 0146-0749 *p. 524* (Sep. 1996).
Manjunath, R., "Inhibition of Thrombin-Induced Platelet Aggregation by Uteroglobin" Biochemical Pharmacology 36 (5):741-746 (Mar. 1987).
Manjunath, R., "Crosslinking of Uteroglobin by Transglutaminase" Biochemical and Biophysical Research Communications 121(11):400-407 (May 1984).
Mesh Database, entry for "Cystic Fibrosis" [online] National Center for Biotechnology Information, National Library of Medicine, NIH, Apr. 8, 2008.
Miele L., "Novel Anti-Inflammatory Peptides From the Region of Higher Similarity Between Uteroglobin and Lipocortin I." Nature 335(6192): 726-730 (Oct. 1988).
Miele, L., "High Level Bacterial Expression of Uteroglobin, A Dimeric Eukaryotic Protein with Two Interchain Disulfide Bridges, in its natural quaternary Structure" Journal of Biological Chemistry 265(11): 6427-6435 (Apr. 1990).
Miele, L., "Uteroglobin: Structure, Molecular Biology, and New Perspectives on Its Function as a Phospholipase A. sub.2 Inhibitor" Endocrine Reviews 8(4):474-490 (Nov. 1987).
Mihal, K., "One gene encoding three proteins with different functions," American Journal of Respiratory Cell and Molecular Biology 5(1):1-3 (Jul. 1991).
Mourot et al., "Comparative Evaluation of Ultrafiltration Membranes for Purification of Synthetic Peptides", Separation Science and Technology, 1989, vol. 24, No. 5 & 6, pp. 353-367, especially pp. 353 and 354.
Mukherjee AB, "Could the Gene Coding for Human Uteroglobin (Clara Cell 10kDa Protein) be a candidate gene for Atopy?" American Journal of Human Genetics 55(3):353-367 (Jan. 1994).
Mukherjee, "Modulation of Cellular Response to Antigens by Uteroglobin and Transglutaminase." Advances in Experimental Biology 231:135-152 (Jan. 1988).
Mukherjee, A. "Phospholipase A.sub.2 Enzymes: Regulation and Physiological Role." Biochemical harmacology 48(1):1-10 (Jul. 1994).
Nomori, H., "Protein 1 and Clara Cell 10-kDa Protein Distribution in Normal and Neoplastic Tissued with Emphasis on the Respiratory System." Virchows Archives 424:517-523 (Jun. 1994).
Nord, M., "Calcium-Dependent Binding of Uteroglobin (PCB-BP/CCSP) Two Negatively Charged Fossil Liposomes." Federation of European Biochemical Societies Letters 374(3): 403-406 (Nov. 1995).
Okutani, R., "Simple and High-Yield Purification of Urine Protein 1 Using Immunoaffinity Chromatography: Evidence for the identity of Urine Protein 1 and Human Clara Cell 10-Kilodalton Protein." Journal of Chromatography 577(1): 25-35 (May 1992).
Olson, "Know your neighbors: Three Phenotypes in Null Mutants of the Myogenic BHLH Gene MRF4." Cell 85(1):14 (Apr. 1996).
Pattabiraman, "Crystal Structure Analysis of Recombinant Human Uteroglobin and Molecular Modeling of Ligand Binding." Annals New York Academy of Sciences 923:113-127 (2000).
Peri, "Expression of Clara Cell 10-kD Gene in the Human Endometrium and its Relationship to Ovarian Menstrual cycle," DNA and Cell Biology, 13(5):495-503 (May 1994).
Peter, W., "Recombinant Rabbit Uteroglobin Expressed at High Levels in E. coli Forms Stable Dimers and Binds Progesterone." Protein Engineering 3(1): 61-66 (Oct. 1989).

(56) References Cited

OTHER PUBLICATIONS

Peteres, "Clinical determinants of abnormalities in pulmonary functions in survivors of the Adult Respiratory Distress Syndrome." American Review of Respiratory Disease 139(5):1163-1168 (May 1989).

Piomelli, D., "Arachidonic Acid in Cell Signaling." Current Opinion in Cell Biology 5(2): 274-180 (Apr. 1993).

* cited by examiner

RECOMBINANT HUMAN CC10 AND COMPOSITIONS THEREOF FOR USE IN THE TREATMENT OF NASAL RHINITIS

CROSS-REFERENCE TO RELATED APPLICATIONS

This application is a continuation of U.S. patent application Ser. No. 12/945,622, filed Nov. 12, 2010, now abandoned, which is a continuation of PCT Application PCT/US2009/043613, filed May 12, 2009, which claims benefit of and priority to U.S. Provisional Patent Application 61/052,861, filed May 13, 2008, the disclosures of each of which is hereby incorporated by reference in its entirety.

FIELD OF THE INVENTION

The present invention relates to methods of reducing airflow obstruction in the nasal passages, clearing a sinus infection, and reducing sinus pain in a patient. More specifically the present invention relates to methods of treating nasal rhinitis, sinusitis and nasal polyposis in patients and compositions useful for the same. Yet more specifically, the present invention relates to methods of treating the above using intranasally-administered recombinant human CC10 and compositions thereof useful for the same.

BACKGROUND

Clara Cell "10 kDa" protein (CC10) or uteroglobin (UG) is a small, homodimeric secretory protein produced by several mucosal epithelia and other organs of epithelial origin (Mukherjee, 1999). CC10 consists of two identical subunits of 70 amino acid residues, each with the "four helical bundle" secondary structure motif, joined in antiparallel orientation by two disulfide bonds between Cys 3 and 69', 3' and 69 (Matthews, 1994; Morize, 1997). The homodimer containing two disulfide bonds appears to be its primary, extracellular active form. In humans, the lung is the main site of CC10 production, while several other organs synthesize smaller amounts of mRNA encoding this protein (Singh, 1987; Sandmoller, 1994). CC10 is an anti-inflammatory and immunomodulatory protein that has been characterized with respect to various interactions with other proteins, receptors and cell types (reviewed in Mukherjee, 2007, Mukherjee, 1999, and Pilon, 2000). Lower levels of CC10 protein or mRNA have been found in various tissue and fluid samples for a number of clinical conditions characterized by some degree of inflammation including asthma (Lensmar, 2000; Shijubo, 1999; Van Vyve, 1995), pneumonia (Nomori, 1995), bronchiolitis obliterans (Nord, 2002), sarcoidosis (Shijubo, 2000), and in patients suffering from chronic rhinitis with recurrent sinusitis and nasal polyposis (Liu, 2004). Pulmonary epithelial cells, the body's primary source for endogenous CC10, are often adversely affected in these conditions, depleted or even ablated (Shijubo, 1999). Indeed, CC10 appears to be an autocrine and/or endocrine required for development of specific sets of non-ciliated respiratory epithelial cells and associated structures (Castro, 2000). Thus, it is still not known whether CC10 deficiency is a cause or an effect of the inflammation and/or the condition.

The obstruction of airflow in the nasal passages, as well as sinus pain and pressure, are known to be causes of significant morbidity in humans suffering from allergic rhinitis, non-allergic rhinitis, sinusitis, and nasal polyposis. Nasal rhinitis is an inflammation of the nasal passages and sinuses in the nasopharygeal cavity. There are two types of rhinitis, allergic and non-allergic. Non-allergic rhinitis is due to viral, bacterial, or other infection, to exposure to inhaled chemicals or other irritants, or may be idiopathic, while allergic rhinitis is due to exposure to inhaled allergens. Allergic rhinitis may be seasonal, such as allergy to tree or grass pollen; or it may be perennial, such as allergy to dust mites and common molds. Rhinitis ranges in severity from mild seasonal discomfort due to itching, sneezing, and nasal discharge for a few hours, days or weeks, to painful and debilitating chronic sinus inflammation that is often associated with recurrent bacterial infection. Chronic sinus inflammation in the presence of bacterial infection is sometimes referred to as chronic rhinosinusitis ("CRS"). CRS, leads to irreversible remodeling and scarring of airway epithelia and sinus tissue. These permanent changes to the nasal tissues result in a vicious cycle in which decreased ability to fight infection, both viral and bacterial, as well as a decreased ability to clear inhaled allergens and irritants, lead to even more exaggerated inflammatory responses, further exacerbating remodeling and fibrosis, and more severe or persistent infections. Theoretically, inflammation is reversible in the absence of infection, and should disappear as soon as the irritant, pathogen, or allergen is cleared from the local tissue. Therefore, the transition from seasonal or mild rhinitis to CRS can be attributed largely to chronic exposure to perennial allergens and/or recurrent bacterial infection of the inflamed nasal and sinus tissue, leaving the infection to persist even after the original rhinitis stimuli (allergen or irritant) is long gone. Indeed, patients with perennial allergies resulting in chronic rhinitis often experience recurrent bacterial infection (sinusitis) as the inflammatory response transitions from an allergen-stimulated response to an infection-stimulated response. These are the patients with severe persistent rhinosinusitis CRS disease and the highest morbidity. Chronic rhinitis, whether allergic or non-allergic, results in excess mucus production in, and swelling of, nasal passages that impairs breathing, disrupts sleep, and predisposes to repeated bacterial sinus infections. The sinus pain and pressure causes significant morbidity in this disease. Bacterial infection, whether acute or chronic, exacerbates these symptoms. In the most severe cases, nasal polyps grow in the nasal airways and slowly obstruct them. These polyps are non-malignant outgrowths of sinus tissue which can only be removed by sinus stripping surgeries. A patient with nasal polyps may undergo sinus stripping periodically since the polyps grow back after each removal.

However, determining whether rhCC10 can alleviate inflammation, and at what dosage, in patients suffering from nasal rhinitis, especially chronic rhinitis and rhinosinusitis, with or without nasal polyposis and in patients suffering from chronic or recurrent bacterial sinus infection has remained elusive. In fact, as shown below, recent work indicates that at dosages known and commonly used, rhCC10 is ineffective:

In a recent Phase II clinical study to evaluation the efficacy of intranasal rhCC10 to suppress nasal inflammation and rhinitis due to seasonal allergy, rhCC10 treatment resulted in a significant worsening of symptoms in one of six efficacy outcome measures compared to placebo (Widegren, et al., 2009). The remaining five efficacy outcome measures showed no difference between rhCC10 and placebo, although all trended in favor of placebo. RhCC10 was inferior to placebo in improving (increasing) peak nasal inspiratory flow and in mitigating rhinorrea caused by administration of aero-allergens. Table 1 shows comparative outcomes of patients while receiving rhCC10 versus outcomes in the same patients while receiving placebo, as measured during the last three days (days 5-7) of each treatment period.

TABLE 1

P-values for statistical differences between rhCC10 and placebo in five clinical outcome measures.

| Efficacy Variable | rhCC10 | Placebo | P-value |
|---|---|---|---|
| Morning TNSS | 1.64 (0.21) | 1.50 (0.25) | .57 |
| Morning PNIF | 136 (7) | 136 (8) | .78 |
| Evening TNSS | 1.37 (0.28) | 1.54 (0.27) | .53 |
| Evening PNIF | 145 (8) | 147 (8) | .93 |
| TNSS-10 min after challenge | 5.67 (0.27) | 5.17 (0.32) | .09 |
| PNIF-10 min after challenge | 93 (6) | 102 (7) | .04* |

*A p-value of <0.05 (less than 0.05) is considered to be a significant difference.
P-values higher than 0.05 are not considered to be statistically significant.
TNSS: Total nasal symptoms score
PNIF: Peak nasal inspiratory flow This proof-of-concept study failed to demonstrate the overall efficacy of rhCC10 given once daily for seven days in this nasal allergen challenge model of seasonal allergic rhinitis. RhCC10, given 1.1 mg in 200 μL per day intranasally, did not favorably affect allergen-induced morning, post challenge or evening symptoms compared with placebo. A higher PNIF reflects greater airflow and a lower PNIF indicates restricted airflow. Morning as well as evening PNIF were unaffected by rhCC10, however, post challenge PNIF was modestly reduced by rhCC10 treatment compared to placebo, which did reach statistical significance. Symptom-scores and PNIF-levels reached in the placebo arm were very similar to those recorded historically in this model. Likewise, markers of inflammation in nasal lavage fluids, including levels of eosinophil cationic protein, myeloperoxidase, and alpha2-macroglobulin, and rhCC10 did not mediate any reduction in these markers compared to placebo. In this model, it has been demonstrated that corticosteroids inhibit morning, post-challenge as well as evening symptoms and these markers of inflammation in nasal lavages (Ahlstrom-Emanuelsson et al., 2002 & 2007) whereas anti-histamines reduce post-challenge symptoms only (Korsgren et al. 2007). Therefore, using this dose, dosing regimen, volume and spray method of intranasal administration, rhCC10 did not demonstrate anti-allergy, anti-inflammatory effects in all six clinical outcome measures or in all three inflammatory markers in nasal lavages.

Currently, most nasal rhinitis and rhinosinusitis are treated with various over-the-counter and prescription medications such as anti-histamines, decongestants, non-steroidal anti-inflammatory agents ("NSAIDS") and various non-pharmacologic nasal sprays and irrigation solutions. Chromium nasal solutions, oral anti-histamines and leukotriene receptor antagonists treat symptoms but provide only a few hours of relief. Nasal oxymetazoline solutions are very effective at opening nasal passages but overuse results in a "rebound effect" and rapid loss of efficacy with worsening of symptoms. Side effects for these types of drugs include sore throat, dehydration of nasal tissues, and constipation, among others.

Furthermore, sinusitis is typically treated with oral antibiotics. Antibiotics range in side effects from mild to severe and can include constipation and other digestive problems, headache, dizziness, rashes, liver, kidney and bladder toxicity, muscle and joint pain, etc. Antibiotics can also cause hypersensitivity reactions, particularly in patients with recurrent sinusitis who have to take antibiotics repeatedly and eventually become allergic to them. Hypersensitivity reactions to antibiotics may occur without warning or previous signs of allergy and may be suddenly lethal.

For severe and/or chronic rhinosinusitis disease, physicians currently prescribe nasal corticosteroids, which reduce inflammation but often lose efficacy after a few weeks or months of continuous therapy. Oral corticosteroids are also efficacious but have many undesirable side effects when used for long periods of time. For example, in adults, cardiovascular complications, including hypertension and stroke, are major side effects of corticosteroid use. In children, corticosteroids impair normal growth and development. In all patients, corticosteroids lower the patient's immune function and leave them susceptible to infection of all types (bacterial, viral, fungal, etc.). Thus, safety is a major consideration in the choice of drugs and drug combinations used to treat, prevent or cure nasal rhinitis, especially chronic rhinosinusitis, nasal polyposis, chronic or recurrent bacterial sinus infection, their associated morbidities and other similar conditions.

There are several formulations, devices, and methods by which drugs may be administered intranasally to treat rhinitis, sinusitis, and rhinosinusitis. One method for administering local intranasal doses of drugs to the nasal passages and sinuses is the use of liquid drug formulations in spray bottle or spray pump devices that are converted to aerosols by being forced through a small aperture and sprayed into the anterior portion of the nasal cavity through each nostril.

Particle sizes generated by the aforementioned devices are in the 5-10 micron range, which maximizes delivery and local deposition of the drug in the nasal mucosa lining the nasopharygeal cavity. The nasal mucosa is comprised of a normally thin layer of mucus that overlays the wet epithelium in the nasal passages and sinuses of the nasopharyngeal cavity. Most 5-10 micron particles sprayed into the nostril will impact the non-ciliated epithelium in the anterior portion of the nasopharyngeal cavity. Once deposited at the site of impaction in the nasal mucosa, drugs may distribute throughout the mucosa and be cleared at various rates through the action of cilia and ciliated epithelial cells located in the posterior two thirds of the nasopharyngeal cavity that push towards the pharynx where the drug and mucus are swallowed. The local action of drugs deposited in the nasal cavity depends upon the particle size delivered, the formulation, and the rate of clearance. These factors affect the efficiency of local delivery and the length of time that the nasopharyngeal mucosa and epithelia are exposed to the drug before it is cleared.

The local action of intranasally administered drugs also depends upon the condition of the nasal mucosa and tissues at the time of delivery. For example, when the nasal passages are blocked by thick mucus, local delivery of drugs is very difficult, if not impossible.

Therefore, it is a significant challenge to find an agent, and a correct dosage for that agent, which alleviates airway obstruction, sinus pain and discomfort for a pro-longed period of time without serious side effects. There is therefore a need for new, more effective or longer-lasting agents and formulations thereof and administration and dosage regimens thereof, particularly in patients with chronic disease.

OBJECTS OF THE INVENTION

The foregoing provides a non-exclusive list of the objectives achieved by the present invention:

It is a primary object of the invention to treat, cure or prevent nasal rhinitis, sinusitis, especially chronic rhinitis and rhinosinusitis, with or without nasal polyposis, in patients using rhCC10.

It is a further object of the invention to alleviate the pain and sinus pressure associated with chronic rhinitis, sinusitis, and rhinosinusitis using rhCC10.

It is a further object of the invention to enable patients with nasal rhinitis or sinusitis to achieve a better quality of sleep using rhCC10.

It is a further object of the invention to administer the rhCC10 to patients by intranasal instillation, nasal lavage or as an intranasal aerosol involving the use of a spray device.

It is a further object of the invention to provide a safe, well-tolerated and effective dosage range of rhCC10 which accomplishes the above objectives and does not significantly suppress the immune response or increase the frequency or severity of adverse events.

It is a further object of the invention to provide a drug-device combination by which rhCC10 can be effectively administered to the nasopharygeal cavity as an aerosol, as a gel, or as a liquid.

It is a further object of the invention to provide a formulation of rhCC10 in specific pharmacologically-acceptable nasal excipients for application in a gel or cream for local administration and prolonged release, using a single use swab applicator.

It is a further object of the invention to provide a formulation of rhCC10 in specific pharmacologically-acceptable nasal excipients for application as an aerosol with particles sizes in the 5-10 micron range for local administration and deposition, using a spray pump or squeeze bottle.

It is a further object of the invention to provide a formulation of rhCC10 in specific pharmacologically-acceptable nasal excipients for application as an aerosol with particles sizes in the 5-10 micron range for local administration and deposition, using a multi-use spray pump dispenser, metered dose inhaler (MDI), or squeeze bottle device.

It is a further object of the invention to provide a formulation of rhCC10 in specific pharmacologically-acceptable nasal excipients for application as an aerosol with particles sizes in the 1-5 micron range for pulmonary administration and deposition, using a single or multi-use spray pump dispenser, metered dose inhaler (MDI), or squeeze bottle device.

It is a further object of the invention to provide a formulation of rhCC10 in specific pharmacologically-acceptable nasal excipients for application as an instillation in a single or multi-dose syringe device.

It is a further object of the invention to provide a formulation of rhCC10 in specific pharmacologically-acceptable nasal excipients for application as an instillation in a nasal lavage solution using a "neti pot" or similar gravity flow lavage device.

It is a further object of the invention to provide rhCC10 itself as a pharmacologically-acceptable nasal excipient for the alleviation of pain, irritation, and discomfort caused by local inflammatory responses at the site of administration of other drugs in the nasopharyngeal cavity.

It is a further object of the invention to provide rhCC10 itself as a pharmacologically-acceptable nasal excipient to enhance the bioavailability of other drugs administered to or via the nasopharyngeal cavity.

It is a further object of the invention to provide rhCC10 as an active ingredient in combination formulations with other drugs for intranasal administration.

The term "pharmacologically-acceptable" is intended to characterize a formulation or combination of excipients that cause no deleterious effects or cause deleterious effects that are known and are, or can be, accepted by regulatory authorities.

SUMMARY OF THE INVENTION

These and other objects, features and advantages are achieved by administering rhCC10 in a dosage range given at appropriate intervals, or in one dose, to treat, cure or prevent nasal rhinitis, sinusitis, rhinosinusitis, and CRS, with or without nasal polyposis. Furthermore, for chronic rhinitis patients rhCC10 offers an even greater benefit in treating, curing or prevention of chronic rhinitis when given in a dosage range at appropriate intervals, or in one dose. Thus, it has now been surprisingly found that rhCC10, which was thought to be ineffective in curing, treating or preventing nasal inflammation, rhinitis, nasal rhinitis, chronic rhinitis, sinusitis and rhinosinusitis, is in fact effective when used in accordance with the invention herein.

These and other objects, features and advantages are also achieved by administering rhCC10 in a dosage range given at appropriate intervals or in one dose where a patient shows one or more of the following: sinus pain and pressure, inability to sleep due to sinus discomfort, chronic rhinitis, rhinosinusitis, and growth or regrowth of nasal polyps.

These and other objects, features and advantages are also achieved by administering rhCC10 such that it does not inhibit platelet aggregation, suppress the immune response, such as in common cold or flu, or increase the frequency or severity of any adverse event.

In certain aspects of the invention, rhCC10 is administered intranasally in a single dose divided about equally between each nostril in a range of 1.5 micrograms to 1.1 milligrams per day, or in multiple doses which taken together achieve this dosage range on a daily basis to treat, cure or prevent severe nasal rhinitis, nasal sinusitis, especially chronic rhinosinusitis, and/or nasal polyposis. In another aspect, an intranasal rhCC10 dose or doses divided about equally between each nostril in a range of 1.5 micrograms to 1.1 milligrams per day can be repeated at appropriate intervals to treat, cure or prevent severe nasal rhinitis, nasal sinusitis, chronic rhinitis with recurrent sinusitis, especially rhinosinusitis, and/or nasal polyposis. In yet another aspect of the invention, rhCC10 is administered intranasally on a daily basis consecutively for seven days, ten days, 14 days, or 21 days.

In yet another aspect of the invention, rhCC10 is administered three times per day, at approximately eight hour intervals in intranasal doses divided about equally between each nostril in a range of 0.5 to 370 micrograms per day. In yet another aspect of the invention, rhCC10 is administered two times per day, at approximately twelve hour intervals in intranasal doses divided about equally between each nostril in a range of 0.75 to 650 micrograms per day.

In yet another aspect of the invention, rhCC10 is administered in a tapered fashion, beginning with three times per day, at approximately eight hour intervals in intranasal doses divided about equally between each nostril in a range of 0.5 to 370 micrograms per day for three days, followed by two times per day, at approximately twelve hour intervals in intranasal doses divided about equally between each nostril in a range of 0.5 to 370 micrograms per day, followed by one time per day in intranasal doses divided about equally between each nostril in a range of 0.5 to 370 micrograms per day. In yet other aspect of the invention, rhCC10 is administered intranasally in accordance with the above aspects but in a dose or doses adding up to between about 15 nanograms and about 10 milligrams.

Whether administered intranasally or otherwise, rhCC10 can be given alone, in conjunction with, before or after other standard rhinitis and sinusitis treatments, including but not limited to intranasal or systemic corticosteroids, NSAIDs (including aspirin, COX-2 inhibitors), pain medications, antibiotics, antivirals, antifungals, decongestants, antihistamines, chromium solutions, nasal lavage, saline nasal lavage, and homeopathic remedies.

In another aspect, rhCC10 can be used as an excipient and/or local anti-inflammatory, and/or local immunosuppressor, to facilitate the local nasal delivery or application for local delivery or systemic absorption of other drugs to the nasal tissues that may or may not irritate or otherwise elicit, or may elicit, an undesired local irritation at the site of application. Thus, rhCC10 may be used as an excipient for other drugs to alleviate or avoid discomfort associated with nasal delivery.

In another aspect, rhCC10 can be used as an excipient or to alleviate the irritation caused by intranasal administration of other drugs for either local or systemic delivery.

In addition, rhCC10 can be formulated as an aqueous solution, a suspension (containing a nasal surfactant excipient), or a gel (such as a hydrogel employing, for example, hydroxymethylcellulose), in order to achieve the proper viscosity for nasal application and local distribution profile in the nasopharyngeal cavity. Likewise, rhCC10 can be formulated in combination with other active ingredients such as antibiotics or other antimicrobial agents, saline nasal lavages, decongestants, mucolytics, LTRA's, β-agonists, bronchodilators, etc.

In another aspect, rhCC10 is formulated as an aqueous solution that is loaded into a nasal spray squeeze bottle, metered dose inhaler or spray pump device. In yet another aspect, rhCC10 is formulated as a suspension in a surfactant that is loaded into a nasal syringe-type application device, a metered dose inhaler, or other nasal application device. Further, in still another aspect, rhCC10 is formulated in a hydrogel, or other form of artificial mucus, and single doses are placed in a single use nasal swab device for intranasal application.

DETAILED DESCRIPTION

The present invention relates to the critical dosages and timing of administration of rhCC10 to treat, cure or prevent nasal rhinitis and sinusitis, especially chronic nasal rhinitis with recurrent sinusitis, chronic rhinosinusitis, and nasal polyposis in humans. The rhCC10 is preferably obtained by the processes described in U.S. Patent Application Publication Nos. US 2003-0109429 and US 2003-0207795 attached hereto at Ex. A & B, respectively, both of which are incorporated by reference in their entirety, or via any other process which yields pharmaceutical grade (meeting FDA requirements) rhCC10. The rhCC10 of the embodiments of the present invention can be administered with, without, before or after other intranasal, pulmonary, or systemic therapy.

Dosages

Preferably, in treating or preventing nasal rhinitis, sinusitis, chronic rhinosinusitis, and nasal polyposis, rhCC10 is administered intranasally, to each nostril 1-3 times per day, for 7-14 days, and every other day thereafter for another 14 days, and thereafter as needed. More preferably, rhCC10 is administered as soon as the patient begins to experience sinus pain and pressure.

To effectuate the desired outcomes which are further described below, reference is made to methods of administration described in the following embodiments:

In one embodiment, a dose or multiple doses of rhCC10 equaling a dose ranging from about 1.5 micrograms to about 1.5 milligrams can be administered. In another embodiment, rhCC10 can be administered in the dose range on a daily basis. In yet another embodiment, rhCC10 can be administered in the dose range on a daily basis for at least seven days consecutively. In still a further embodiment, rhCC10 can be administered in the dose range on a daily basis for at least 14 days consecutively. In still another embodiment, rhCC10 can be administered in the dose range every other day for 30 days consecutively. In yet another embodiment, rhCC10 can be administered in tapered dosages daily for ten consecutive days, said tapered dosages comprising a high dose at each administration for the first three days, an intermediate dose at each administration for the second three days, and a low dose at each administration for the last four days. In yet still another embodiment, rhCC10 can be administered in the dose range or in tapered doses up to three times per day, approximately every eight hours.

In another embodiment the above doses of rhCC10 can be administered intranasally to the patient. In yet another embodiment, the above doses of rhCC10 can be administered to the patient as an aerosol, by intranasal instillation, or by deposition of a gel or cream in nasal passages. In a further embodiment, rhCC10, in accordance with the methods described above, can be administered prior to, during or after an oral or intranasal decongestant, anti-histamine, corticosteroid, mucolytic, expectorant, mucus suppressor, surfactant, bronchodilator, vasoconstrictor, sinus pain analgesic, or other typical therapy. In still another embodiment, rhCC10, in accordance with the methods described above, can be administered to treat or prevent nasal rhinitis, nasal sinusitis, chronic rhinosinusitis, or nasal polyposis in a patient.

The doses of rhCC10 and application methods described above can be administered daily, more than once daily, three times daily, every other day or in a tapered fashion depending upon the severity of disease being treated, the patient's overall health, and whether an acute or chronic condition is being treated. For example, the more severe the disease condition, the higher the amount of rhCC10 would be required to effectively treat the disease. For maintenance therapy of chronic disease, for example, to prevent an exacerbation of nasal rhinitis, nasal sinusitis, or nasal polyposis, lower doses would be used. It is understood that a physician would be able to monitor and adjust doses, formulations, and application methods as needed based on the patient's symptoms and responses to therapy and within the parameters and dose ranges described in the embodiments of the present invention.

Formulations rhCC10 is maximally effective when applied directly to the local nasal epithelium, for example by use of a liquid formulation in a spray bottle, spray pump, or lavage. Therefore, it is sometimes necessary to use fast-acting local mucolytics, anti-histamines, and/or decongestants, as well as physical methods such as inhaling moist warm air, hot compresses applied to the face, and salt water nasal lavage to open up the nasal passages before rhCC10 can be applied effectively to the nasal epithelia.

Intranasal instillation is another method for administering rhCC10 that can be accomplished using rhCC10 in either a liquid or gel formulation. The gel dosage formulation provides the advantage of better local dosing over a longer period of time by retaining the dose of rhCC10 in the local nasal area in which it was swabbed longer, whilst liquid dosages may be partially swallowed following instillation due to normal nasal drainage resulting in much shorter local exposures and smaller local doses. However, intranasal instillation of a liquid dosage form by nasal lavage, using a "neti pot" type of device, confers the advantage that the dose is more immediately distributed over a larger surface area in the nasal tissues and sinuses, than a local application gel formulation.

rhCC10 can be formulated with several nasal excipients for intranasal delivery. These include excipients to adjust the pH of the drug, to buffer the drug to maintain solubility, to act as preservatives or enhance preservatives for prevention of microbial growth and/or transfer, to adjust the tonicity, solubility, or viscosity of the drug, to enhance penetration or permeation of the drug (systemic delivery), to modify the local bioavailability and half-life of the drug (increase viscosity), to reduce toxicity, to suspend insoluble drugs, and to alter the taste of the formulation. Table 2 contains a non-exclusive list of exemplary excipients and their functions in intranasal formulations of rhCC10. Any single excipient or combination of excipients can be used to formulate rhCC10 for intranasal administration.

TABLE 2

Examples of Excipients for Intranasal Formulations

| Excipient | Function |
| --- | --- |
| Acids (hydrochloric, acetic, citric) | pH adjustment, buffer |
| Sodium hydroxide | pH adjustment |
| Sodium & potassium salts (Sodium acetate, sodium citrate, sodium phosphate, potassium phosphate) | Buffer |
| Edetate disodium | Preservative enhancer, Metal chelator |
| Benzalkonium chloride | Preservative |
| Benzethonium chloride | Preservative |
| Benzyl alchohol (aka phenylcarbinol, etc.) | Preservative |
| Chlorobutanol | Preservative |
| Methylparaben | Preservative |
| Phenylethyl alcohol | Preservative |
| Phenylmercuric acetate | Preservative |
| Propylparaben | Preservative |
| Thimerosal | Preservative |
| Sodium or potassium chloride | Adjust tonicity (make isotonic) |
| Microchrystalline cellulose | Adjust viscosity |
| Na carboxymethylcellulose | Adjust viscosity |
| Hydroxyethylcellulose | Adjust viscosity |
| Ethanol | Solvent |
| Glycerol | Solvent/Adjust tonicity |
| Glycine | Solvent/Adjust tonicity |
| Dextrose | Adjust tonicity |
| Polyethylene glycol (PEG) | Solvent |
| Propylene glycol | Solvent |
| Glyceryl dioleate | Solvent |
| Glyceryl monoleate | Surfactant/emulsifier (suspend lipophilic drugs) |
| Lecithin | Surfactant/emulsifier (suspend lipophilic drugs) |
| Polysorbate 20 & 80 (aka Tween 20 & 80) | Surfactant/emulsifier (suspend lipophilic drugs) |
| Triglycerides | Multiple |
| Menthol | Modify flavor |
| Saccharin sodium | Modify flavor |
| Sorbitol | Modify flavor |
| Chitosan | Permeation enhancer |
| Cyclodextrin | Permeation enhancer |
| Bile salts | Permeation enhancer |
| Liposomes | Permeation enhancer |
| Starch microspheres | Permeation enhancer |
| Glycerrhizin | Permeation enhancer | rhCC10 can also be formulated in combination with other drugs, artificial mucus, or other active ingredient for intranasal administration. Drugs with which rhCC10 can be formulated for intranasal administration include, but are not limited to, local or systemic antimicrobial agents (antivirals, antibacterials, antifungals), decongestants, anti-histamines, mucolytics, expectorants, leukotriene receptor antagonists, bronchodilators, beta$_2$-adrenergic receptor agonists, local-acting vasoconstrictors (such as oxymetazoline), anti-inflammatory agents, and analgesic agents. Still other drugs with which rhCC10 can be formulated for intranasal administration for local or systemic effects include anti-inflammatory agents, beta$_2$-adrenergic receptor agonists, anti-cancer agents, anti-angiogenic agents, anti-fibrotic agents, immunomodulatory agents, vaccines, metabolic agents, analgesics, neuroleptic agents, anesthetics, agents for depression and other psychiatric disease (mental health), anti-addiction agents, homeopathic remedies, herbal preparations, vitamins and minerals and the like.

rhCC10 is compatible with most non-reactive chemicals and drugs, including hydrophilic and hydrophobic chemicals, nucleic acids and nucleic acid analogs, proteins and peptides, carbohydrates, lipids and phospholipids, etc. As a secretoglobin critically involved in transport of substances in epithelial cells, rhCC10 is ideally suited to enhance the delivery of other drugs via the nasal passages. rhCC10 can also act as a local anti-inflammatory agent that can be used as an excipient to suppress painful local nasal responses at the site of administration of other drugs, such as, for example, chemotherapeutic agents and drugs that produce a "burning sensation" upon administration.

A key parameter relevant to drug efficacy associated with intranasally administered rhCC10 is the concentration of the rhCC10 itself. Formulations in which the rhCC10 concentration is too high (i.e. above 2 mg/ml) have demonstrated null or even detrimental effects, as evidenced by the clinical outcomes described in the Background. The rhCC10 formulation was 5.6 mg/ml and was applied directly to the patient's nostrils (Widegren, et al. 2009). Conversely, in example 4, in which the rhCC10 concentration was 250-262 micrograms/ml, a clinical benefit was conferred. In an unrelated experiment, pre-term lambs treated with 5 mg/kg of body weight using a 5.5 mg/ml formulation of rhCC10, administered by intratracheal instillation, suffered from severe hypoxia and ¾ animals died of respiratory failure within four hours of drug administration, while none of the four placebo treated animals died (unpublished; Ikegami, M., Univ of Cincinnati). In contrast, when the same formulation of rhCC10 was diluted to 2 mg/ml and administered via intratracheal instillation to intubated pre-term lambs, the animals showed various benefits from receiving the drug compared to placebo (Miller, 2005a, 2005b, 2007; Shashikant, 2005). Without being bound to any particular theory, the phenomenon may be related to the very high sphere of hydration for rhCC10, that is, the number of water molecules coordinated by CC10 is higher than the average protein. Administration of high concentrations of CC10 to mucosal and other bodily fluids may result in the "subtraction" or loss of water from the local fluids, thereby causing a local dehydration and detrimental disruption in the equilibria between substances in the local biological milieu. Alternatively, or in conjunction with the preceding, an acute local over-abundance of CC10 may also result in desensitization of cells and tissues to the presence of CC10, effectively reducing the potency of the drug rather than increasing the pharmacologic effect. In some cases, feedback inhibition of a pathway or set of pathways involving a particular metabolite or mediator may actually result in the opposite effect (activation versus suppression and vice versa) than may be observed at lower doses of the metabolite or mediator. A cutoff for rhCC10 formulations intended to be administered to nasal and other mucosal surfaces by intranasal, intratracheal or other local/topical administration is 2 mg/ml, above which rhCC10 is not efficacious and can even be detrimental.

The following detailed examples are illustrations of embodiments. It should be clear that these are not intended to limit the scope of the present invention.

EXAMPLE 1

Intranasal Administration of rhCC10 to Allergic Rhinitis Patients

RhCC10 was produced in E. coli bacteria and purified by a process (Claragen, Inc., College Park, Md.), described in U.S. Application Publication Nos. US 2003-0109429 and US 2003-0207795, both of which are incorporated by reference in their entirety. The protein for the study was provided as a >98% pure solution of recombinant human CC10 homodimer. The biological activity of each batch was compared using a proprietary secretory $PLA_2$ inhibition assay, described in U.S. Application Publication Nos. US 2002-0169108 which is incorporated herein by reference.

In the nasal allergen challenge model, patients with known seasonal allergies to known allergens were subjected to instillation of an allergen solution into the nasopharyngeal cavity on seven consecutive days. In order to minimize safety risks the amount of allergen instilled was carefully calibrated in each patient to elicit a mild local allergic response that is quantitated using four main outcome parameters over the seven day challenge period. These parameters include; 1) total nasal symptom scores, 2) peak nasal inspiratory flow, 3) quantitation of biomarkers in nasal lavages, and 4) response to histamine challenge.

A total of 35 patients with seasonal allergies to tree pollens completed a placebo-controlled, randomized, blinded, cross-over nasal allergen challenge study of rhCC10 versus placebo at the Lund University Hospital in Lund, Sweden. The purpose of the study was to determine the safety, tolerability and efficacy of intranasal administration of recombinant human Clara Cell 10 kDa (rhCC10) protein in subjects with allergic rhinitis. In order to investigate whether intranasal administration of rhCC10 could mitigate the nasal rhinitis symptoms caused by nasal allergen challenge.

Patient responses to nasal allergen challenges in the absence of rhCC10 were first measured and baseline data recorded. A total of 39 patients were screened for inclusion in the study. All patients were male subjects, aged 18-50 years, with Body Mass Index between 18 and 28 $kg/m^2$, and a history of birch and/or timothy pollen-induced seasonal allergic rhinitis for at least the previous 2 years and otherwise healthy. Each patient had elevated specific IgE or at least one positive skin prick test (SPT) to at least one aero allergen (eg. timothy or birch pollen) and each patient exhibited symptoms provoked by the allergen with a corresponding elevated specific IgE or positive SPT. Subjects were excluded from the study if they had perennial allergy (e.g. chronic rhinitis), except for cat and/or dog sensitivity under the condition that these subjects were not exposed to cats and dogs. Subjects were also excluded if they had other nasal disease (eg. structural abnormalities of the nose, rhinosinositis, or nasal polyposis), any upper respiratory tract infection during the period of 2 weeks before the start of the study, were currently receiving treatment or had received treatment within 4 weeks of enrolment with intranasal, inhaled or systemic glucocorticosteroids, β2-adrenergic receptor agonists, or any other anti-inflammatory medication, or had a bacterial or fungal infection within the past month prior to enrollment. A summary of patient characteristics and baseline data is given in Table 2.

TABLE 2

Summary of Demographic and Baseline Data

| Age (years) | Mean (SD) | 26.1 (5.5) |
|---|---|---|
| | Range | 19-48 |
| Race | Caucasian | 39 |
| Gender | Male | 39 |
| Body weight (kg) | Mean (SD) | 81.1 (10.3) |
| Height (cm) | Mean (SD) | 182.6 (7.2) |
| Body mass index (BMI) | Mean (SD) | 24.3 (2.53) |

TABLE 2-continued

Summary of Demographic and Baseline Data

| | | |
|---|---|---|
| Systolic blood pressure | Mean (SD) | 121.4 (9.2) |
| Diastolic blood pressure | Mean (SD) | 77.4 (5.9) |
| Pulse rate | Mean (SD) | 68.8 (8.2) |
| Ear, nose and throat | Normal | 38 |
| | Abnormal | 1 |
| Cardiovascular | Normal | 39 |
| Respiratory | Normal | 39 |

Patients were initially screened for their responses to tree pollen allergens to determine the amount of allergen administered during the challenge periods which was calibrated based on individual patient responses. A physical examination was given, including ear, nose and throat examination and vital signs. Then a nasal allergen challenge was performed in order to establish the allergen dose which resulted in at least 5 sneezes and/or a symptom score of at least 2 on a scale of 0-3 for either the symptoms of nasal congestion or rhinorrea. Rhinorrea is defined as a discharge from the nasal mucus membranes and is typically watery. All allergen administrations were performed in the clinic by hospital staff. In order to estimate, for each individual, the symptom-producing, tolerable, and repeatable allergen dose for the nasal challenge series, a titration procedure was performed in all subjects. The allergen (birch or timothy pollen) that induced the most significant wheal reaction in the skin prick test was chosen for the nasal titration. Increasing doses of allergens (Alutard®, ALK, Denmark) was administered at 10-min intervals using a nasal spray-device. The spray-device delivered 100 µl per actuation, and one puff was sprayed into each nostril resulting in effective doses of 100, 300, 1000, and 3000 SQ-Units per nasal cavity. This scheme was followed until the patient responded acutely with at least five sneezes and/or a symptom score of at least 2 or more on a scale from 0 to 3 for either of the symptoms nasal blockage and runny nose. The allergen dose that produced this effect was chosen for the daily allergen challenge series during the first and second treatment periods (eg. cohorts.) The type and amount of allergen administered to each patient is shown in Table 3.

TABLE 3

Selection of allergen and number of sneezes at allergen titration per subject

| Subject | Selection of allergen (Histamine/ Birch ) | 100 SQ-Units | 300 SQ-Units | 1000 SQ-Units | 3000 SQ-Units |
|---|---|---|---|---|---|
| 1 | Timothy | 6 | — | — | — |
| 2 | Timothy | 3 | — | — | — |
| 3 | Timothy | 0 | 0 | 0 | 0 |
| 4 | Timothy | 1 | 1 | 4 | 6 |
| 5 | Timothy | 0 | 2 | — | — |
| 6 | Timothy | 0 | 0 | 0 | — |
| 7 | Timothy | 1 | 5 | — | — |
| 8 | Timothy | 3 | 4 | 0 | — |
| 9 | Birch | 0 | 4 | — | — |
| 10 | Timothy | 10 | — | — | — |
| 11 | Timothy | 0 | — | — | — |
| 12 | Timothy | 0 | 3 | — | — |
| 13 | Timothy | 0 | 0 | — | — |
| 14 | Birch | 3 | 7 | — | — |
| 15 | Timothy | 0 | 1 | — | — |
| 16 | Timothy | 1 | — | — | — |
| 17 | Timothy | 2 | 5 | — | — |
| 18 | Timothy | 3 | 0 | — | — |
| 19 | Birch | 0 | 0 | 0 | — |
| 20 | Timothy | 0 | 0 | 4 | — |
| 21 | Timothy | 4 | 4 | — | — |
| 22 | Timothy | 3 | — | — | — |
| 23 | Birch | 1 | 10 | — | — |
| 24 | Birch | 3 | — | — | — |
| 25 | Birch | 4 | 4 | — | — |
| 26 | Birch | 0 | — | — | — |
| 27 | Timothy | 4 | 2 | — | — |
| 28 | Timothy | 0 | 0 | 0 | — |
| 29 | Birch | 0 | 0 | 0 | 1 |
| 30 | Timothy | 9 | — | — | — |
| 31 | Timothy | 11 | — | — | — |
| 32 | Timothy | 1 | 1 | 2 | — |
| 33 | Birch | 0 | 0 | 2 | — |
| 34 | Timothy | 2 | 2 | — | — |
| 35 | Timothy | 6 | — | — | — |
| 36 | Timothy | 1 | 7 | — | — |
| 37 | Timothy | 0 | 3 | — | — |
| 38 | Birch | 0 | 5 | — | — |
| 39 | Timothy | 0 | 0 | 3 | — |

The study was performed during the pollen-free winter months. The study was blinded and placebo-controlled in that doctors and patients were not aware of whether they were receiving rhCC10 or placebo. The study was randomized in that patients were randomly assigned to either the rhCC10 or placebo treatment groups. The study was cross-over design in that each patient was treated in two seven day cohorts separated by a washout period of 3-5 weeks. Each patient completed a cohort in which they received rhCC10 and one in which they received placebo. Patients were allowed to take several types of non-steroidal medications, as needed, to relieve their nasal and sinus discomfort during the treatment period. Analgesics (including aspirin but not ibuprofen) and antibiotics were allowed, and Clarityn® (Claritin™) 10 mg, was allowed in case of severe allergic symptoms and was provided by the clinic.

The test agents, placebo and rhCC10, were placed in 10 ml glass vials, labeled numerically so that doctors and patients in the clinic would not be able to distinguish between them. A key was maintained in the hospital pharmacy and doctors were to be informed of the identity of each vial only in the event of an adverse event in which the doctor would need the information to treat the patient. A disposable medical nasal spray device, manufactured by Valois Pharm (France), was connected to the 10 mL vials at the clinical site just before administration. This device consisted of a pump (VP7/100S 18PH), an actuator (PR147) and a cap (B25/A). Placebo consisted of sterile, unbuffered 0.9% sodium chloride. The rhCC10 was in sterile unbuffered 0.9% sodium chloride at a concentration of 5.6 mg/ml. Both placebo and rhCC10 appeared as clear, colorless, odorless liquids that could not be readily distinguished. A total of 100 microliters of placebo or rhCC10 was administered to each nostril of each patient on each day of treatment for a total of seven consecutive days of treatment in each treatment period. All allergen and test agent administrations were performed in the clinic by hospital staff. The total daily dose of rhCC10 was 1.1 milligrams per day, administered in a single dose as an aerosol sprayed in a 100 microliter volume to each nostril, or 0.56 milligrams per nostril. The rhCC10 was administered 15'-30' prior to administration of allergen.

The outcomes were measured as follows:
1. Total Nasal Symptom Score (TNSS)

Nasal symptoms, including nasal congestion, rhinorrea and sneezy/itchy nose were scored by the patients and recorded in the patient diary prior to administration of study medication in the morning (rating symptoms during the preceding 12 h, but disregarding possible symptoms the first 15 minutes post study medication). TNSS was recorded 15 minutes after each allergen challenge. In addition, symptoms were scored in the evening (again reflecting symptoms, during the preceding 12 h, excepting symptoms directly post dosing). The symptoms were each scored according to the following: 0=no symptoms, 1=mild symptoms, 2=moderate symptoms, 3=severe symptoms. The scores were added to constitute a total score, per time point, which ranged from 0 to 9. Mean nasal symptom scores, for morning recordings, for recordings 10 minutes after allergen challenge, and for evening recordings, respectively, of the last three days of each allergen challenge period was used in the statistical analysis.

2. Peak Nasal Inspiratory Flow (PNIF)

PNIF was measured by the patients before the intake of the drug in the morning, 10 minutes after the allergen challenge, and in the evening. The measurements were carried out using a PIF-meter (Clements-Clarke, Harlow, U.K.) equipped with a facial mask. Patients stood up during the procedure, placed the mask snugly over the face with both hands, closed the mouth and inhaled through the nose. They recorded the value and returned the device to a reading of 30, then repeat the procedure 2 more times. The highest value of the three measurements was recorded in the diary. Similar to the nasal symptom score, PNIF recordings, per time point, of the last three days of each allergen challenge period were used in the statistical analysis.

EXAMPLE 2

Co-Administration of Medications

A total of ten patients in both the placebo and rhCC10 groups required rescue medications to treat their discomfort and allergy symptoms while on the protocol. As can be seen from Table 5, a variety of local and systemic drugs for relief of intranasal symptoms were taken, including anti-inflammatory agents, allergy medications, anti-histamines, corticosteroids (Flutide), and oxymetazoline.

TABLE 5

Co-administration of rescue medications in patients receiving placebo or rhCC10

| Subject | Treatment | Day | Medication (trademark/INN) |
|---|---|---|---|
| 3 | rhCC10 | 2 | Clarityn ®(Claritin ™)/loratadin |
|  |  | 6 | Clarityn ®(Claritin ™)/loratadin |
|  |  | 7 | Neseril/oximetazolin |
| 3 | placebo | 4 | Clarityn ®(Claritin ™)/loratadin |
| 5 | rhCC10 | 5 | Loratadin/loratadin |
| 6 | placebo | 2 | Alvedon/paracetamol |
| 12 | placebo | 3 | Loratadin/loratadin |
| 13 | placebo | 3 | Loratadin/loratadin |
| 15 | placebo | 3 | Loratadin/loratadin |
| 18 | placebo | 5 | Clarityn ®(Claritin ™)/loratadin |
|  |  | 6 | Loratadin/loratadin |
| 25 | rhCC0 | 1 | Alvedon/paracetamol |
|  |  | 5 | Loratadin x2/loratadin |
|  |  | 7 | Flutide Nasal/flutikason |
| 25 | placebo | 7 | Antihistamin intake after evening PNIF |
| 26 | rhCC10 | 5 | Loratadin/loratadin |
|  |  | 6 | Loratadin/loratadin |
| 38 | rhCC10 | 5 | Clarityn ®(Claritin ™)/loratadin |
|  |  | 7 | Kestine/ebastin |

Loratadin is a non-sedating antihistamine, paracetamol, is an analgesic and antipyretic, flutikason (fluticasone) is a corticosteroid anti-inflammatory agent, oxymetazoline is a selective alpha-1 agonist and partial alpha-2 agonist topical decongestant, and ebastin is a non-sedating $H_1$ antihistamine. These patients did not experience any significant AEs as a result of co-administration of these other agents simultaneously with the rhCC10, therefore, the combination of rhCC10 with these drugs is safe and pharmacologically-acceptable.

EXAMPLE 3

Safety and Tolerability of Intranasal Administration of rhCC10

As part of the safety assessment for this proof of concept intranasal administration of rhCC10 in humans adverse events (AEs) and serious adverse events (SAEs) were monitored, recorded and reported. The clinical investigator was responsible for the detection and documentation of events meeting the criteria and definition of an AE or SAE. An AE is any untoward medical occurrence in a subject or a clinical investigation temporally associated with the use of the investigational drug whether or not the event is considered to have a causal relationship with the drug. In this trial, a pre-existing condition (i.e., a disorder present before the AE reporting period started and noted on the pre-treatment medical history/physical examination form) was not reported as an AE unless the condition worsened or episodes increased in frequency during the AE reporting period. Serious adverse events were defined as any untoward medical occurrence that, at any dose; 1) results in death, 2) is life-threatening, 3) requires hospitalization or prolongation of an existing hospitalization, 4) results in disability/incapacity, 5) is a congenital anomaly/birth defect, 6) is an important Other Medical Event (OME), and 7) all grade 4 laboratory abnormalities. The AE reporting period for began upon receiving the first dose of investigational medication and ended at the 2-week post discontinuation of investigational medication visit (follow-up visit).

No SAE's occurred during the study. Overall, a total of 15 adverse events were reported in subjects in both the placebo and rhCC10 treatment groups. All AEs were rated as mild in severity. In each group, 11 of 15 AEs were rated as non-assessable with respect to relatedness to study drug while four of 15 AEs in each group were rates as unlikely to be related to study drug. A summary of AEs for each patient receiving placebo is given in Table 6 and for those receiving rhCC10 at the time of the AE are given in Table 7.

TABLE 6

List of adverse events for patient receiving placebo

| Patient number | Description | Maximum intensity | Reported as serious? | Relationship to trial drug |
|---|---|---|---|---|
| 6 | Headache | 1 = mild | 0 = No | 1 = unlikely |
| 12 | Gastric influenza | 1 = mild | 0 = No | 4 = not assessable |
| 12 | Gastric influenza | 1 = mild | 0 = No | 4 = not assessable |
| 15 | Ear pain | 1 = mild | 0 = No | 1 = unlikely |
| 15 | headache | 1 = mild | 0 = No | 4 = not assessable |
| 15 | fatigue | 1 = mild | 0 = No | 4 = not assessable |
| 15 | ear pain | 1 = mild | 0 = No | 4 = not assessable |
| 20 | Sore throat | 1 = mild | 0 = No | 4 = not assessable |
| 20 | Common cold | 1 = mild | 0 = No | 4 = not assessable |
| 25 | Headache | 1 = mild | 0 = No | 1 = unlikely |
| 26 | Sore throat | 1 = mild | 0 = No | 4 = not assessable |
| 27 | stomach ache | 1 = mild | 0 = No | 1 = unlikely |
| 29 | common cold | 1 = mild | 0 = No | 4 = not assessable |
| 31 | Fever | 1 = mild | 0 = No | 4 = not assessable |
| 38 | urticaria | 1 = mild | 0 = No | 4 = not assessable |

TABLE 7

List of adverse events for patient receiving rhCC10

| Patient number | Description | Maximum intensity | Reported as serious? | Relationship to trial drug |
|---|---|---|---|---|
| 1 | Common cold | 1 = mild | 0 = No | 4 = not assessable |
| 2 | Common cold | 1 = mild | 0 = No | 1 = unlikely |
| 2 | Common cold | 1 = mild | 0 = No | 1 = unlikely |
| 7 | Sore throat | 1 = mild | 0 = No | 1 = unlikely |
| 16 | fatigue | 1 = mild | 0 = No | 4 = not assessable |
| 16 | fatigue | 1 = mild | 0 = No | 4 = not assessable |
| 23 | Headache | 1 = mild | 0 = No | 4 = not assessable |
| 23 | Common cold | 1 = mild | 0 = No | 4 = not assessable |
| 26 | Common cold | 1 = mild | 0 = No | 4 = not assessable |
| 28 | tired | 1 = mild | 0 = No | 4 = not assessable |
| 28 | tired | 1 = mild | 0 = No | 4 = not assessable |
| 28 | headache | 1 = mild | 0 = No | 4 = not assessable |
| 32 | Headache | 1 = mild | 0 = No | 4 = not assessable |
| 38 | ague | 1 = mild | 0 = No | 4 = not assessable |
| 39 | Mild cold | 1 = mild | 0 = No | 1 = unlikely |

Therefore, intranasal rhCC10 administration was found to be safe and well-tolerated in humans when given once daily as an aerosol in a divided dose of 1.1 milligrams, 0.56 milligrams per nostril, for seven consecutive days.

EXAMPLE 4

Intranasal Administration of rhCC10 to a Patient with Chronic Rhinitis and Recurrent Sinusitis (aka Chronic Rhinosinusitis)

An 11 mg (2 mls) aliquot of rhCC10 was added to a soft plastic squirt bottle containing 42 mls of sterile 0.65% saline containing disodium and monosodium phosphate, and phenylcarbinol (preservative) plus benzylkonium chloride (preservative), or 0.1% thimerosol (also a preservative), creating a 250 microgram/ml solution of rhCC10. The patient self-administered the rhCC10 by inserting the applicator end of the bottle to the nose, such that the aperture that dispenses the drug is held inside the nostril, and simultaneously squeezing and inhaling. A simple aerosol is created when the bottle is rapidly squeezed, forcing liquid through a small pinhole at the top of the nasal applicator end. The volume and dose delivered depends upon the rapidity of the squeeze and force exerted. Volumes ranging from 25-500 microliters, corresponding to 6.6-131 micrograms of rhCC10, are typically dispensed. When the squeeze is harder and larger volumes are delivered, the nasal passages are lavaged and part of the dose may be swallowed or flow into the trachea over a period of several minutes.

In this example, rhCC10 was administered to a patient suffering from episodic and/or chronic sinus pain due to chronic rhinosinusitis, stemming from perennial allergies, with recurrent bacterial sinus infections. The patient's history includes; 1) antibiotics prescribed from two to twelve times per year for sinus infection in the past six years, 2) intranasal corticosteroids prescribed and taken as needed for the past six years, and 3) non-prescription analgesics, decongestants and anti-histamines taken daily to relieve sinus pain, nasal and chest congestion, and enable the patient to sleep through the night. RhCC10 was a useful substitute and adjunctive therapy for the patient in the following doses, dosing regimen, formulations, and drug-device combinations.

In the first dosing regimen, the patient suffered from a painful bacterial sinus infection for three days prior to self-administering the rhCC10 from the squirt bottle, with two squirts per nostril, three times per day for three days. The total daily dose intake using this method ranged from 78.6-1,572 micrograms total (39.3-786 micrograms per nostril), corresponding to 1.1 micrograms/kg-22.5 micrograms/kg of body weight per day in the average 70 kg patient. The patient then tapered the dosing down to twice per day for two days (52.4-1,024 micrograms daily total (26.2-512 micrograms per nostril), corresponding to 749 nanograms/kg-14.6 micrograms/kg per day in the average 70 kg patient), and then to once per day for two days (26.2-524 micrograms daily total, corresponding to 374 nanograms/kg-7.5 micrograms/kg per day in the average 70 kg patient). After one week of tapered dosing regimen with intranasal rhCC10, the patient discontinued use. The patient's sinus pain, rhinitis and bronchitis symptoms (nasal congestion, sneeze, cough, airway constriction and chest congestion), and sleeplessness, disappeared within 24 hours of initiation of treatment and did not return for at least six weeks following the final dose of rhCC10. Intranasal rhCC10 was safe and well tolerated in the patient, although some drying of nasal mucous membranes was experienced.

EXAMPLE 5

Intranasal Administration of rhCC10 to a Patient to Prevent Recurrent Sinusitis

In a second dosing regimen, the patient received rhCC10 in the formulation and spray bottle of Example 4, twice per day, in the morning and evening, starting within 12 hours of sensing the first sinus pain. The sinus pain was associated with the recurrence of a bacterial sinus infection that had been treated for 14 days with a powerful broad-spectrum antibiotic (eg. Levaquin), during which time the pain abated, but returned within four days of ending the antibiotic. Known side effects associated with the antibiotic occurred in the patient, including constipation and irritable bowels, chest pain, dizziness, transient numbness and tingling in the extremities, extreme sunburn, and increased susceptibility to bruising. As a result, the doctor advised the patient to avoid further use of the antibiotic. The patient then used rhCC10 with over-the-counter decongestants to treat the symptoms associated with the recurrent sinus infection. Within 24 hours of the first dose, the nasal pain and congestion disappeared. The patient continued to administer the rhCC10 twice per day for one week, then decreased to once per day for one week, then discontinued therapy. The bacterial infection did not recur for at least six weeks following intranasal rhCC10 therapy.

EXAMPLE 6

Intranasal Administration of rhCC10 for Maintenance

Maintenance therapy with rhCC10 to prevent sinus pain and infection, often arising from seasonal or perennial allergy and exposure to airborne allergens, is also possible. Daily intranasal administration of rhCC10, at a formulation concentration not to exceed 500 micrograms/ml (preferably not to exceed 250 micrograms/ml), in doses of 26.2-524 micrograms total, given in single or multiple actuations per nostril, corresponding to 374 nanograms/kg-7.5 micrograms/kg of body weight) for up to two and one half months would safely control chronic rhinitis symptoms, rhinosinusitis, nasal and chest congestion, sinus infection and pain, and sleeplessness, and prevent the need for antibiotics, analgesics (NSAIDS such as aspirin, ibuprofen), decongestants, anti-histamines, and sleep-inducing drugs.

Using these methods, formulation, dose, dosing regimen, and drug-device combinations, rhCC10 was efficacious in the alleviation of symptoms associated with chronic rhinitis and bacterial sinus infection (aka chronic rhinosinusitis). In still other instances of severe or recurrent sinus infection, several other antibiotics (Amoxicillin, Zithromax, Biaxin, etc.) were used to contain bacterial growth while rhCC10 alleviated the pain and symptoms. For mild infections and to prevent severe painful infections, rhCC10 was used without an antibiotic, thus, sparing the patient the negative side effects associated with the antibiotic. No adverse events were associated with potential interactions between rhCC10, decongestants, antihistamines, and antibiotics. Thus, over the counter decongestants and antihistamines and antibiotics commonly prescribed for nasal sinusitis were either avoided entirely or used safely in conjunction with rhCC10 to alleviate moderate to severe nasal symptoms.

EXAMPLE 7

Intranasal Administration of rhCC10 for Treatment of Corticosteroid-Refractory, Antibiotic Resistant, Acute Sinus Infection The patient suffered from a severe ongoing sinus infection, characterized by pain, pressure, disruption of sleep, loss of blood pressure upon standing, and inability to walk. The patient had no allergies to airborne allergens (seasonal or perennial) and the infection occurred in the month of January when no seasonal allergens were present. The diagnosis and severity of the sinus infection was verified by CT scan. Prior to receiving rhCC10, the patient had been on antibiotics for 5 weeks (amoxicillin; 500 mg/day; 10 days; then augmentin, 4 grams/day for 3 weeks) and on intranasal corticosteroid treatment for 10 days (fluticasone propionate). Despite these treatments, he remained in considerable pain, with pressure throughout his sinuses, and facial edema (puffiness). Immediately prior to receiving rhCC10, both sides of his nasal septum were blood red and contained readily visible dilated capillaries, indicating the presence of severe local inflammation. A 250 microgram/ml solution of rhCC10 in 0.65% saline containing disodium and monosodium phosphate, phenylcarbinol (preservative) and benzylkonium chloride (preservative) was then administered in a single intranasal dose as a spray into each nostril at a dose of approximately 20-50 micrograms per nostril. Approximately 12 hours after receiving the single intranasal dose of rhCC10, his nasal septum was a normal dusky purple with no dilated capillaries visible, indicating a profound local anti-inflammatory effect. The patient continued on rhCC10, twice daily, for 7 days, noting decreased sinus pain and pressure symptoms. The dosing regimen of rhCC10 was to be tapered from two squirts per nostril, twice per day for 3 days, to one squirt per nostril twice per day for 3 days, to one squirt per nostril once per day for 3 days. The patient continued with this regimen for 4 days. However, it was noted on day 5 that the patient still had intense pain in the ethmoid sinus, which is difficult to access with a nasal spray. Thereafter, the rhCC10 was administered on the same schedule by a lavage technique to increase access of rhCC10 to the surfaces of the ethmoid sinus region. In the lavage method, a total dose of 250 micrograms of rhCC10 (i.e. 1 ml of the 250 microgram/ml solution) was added to 118 mls (½cup; 4 fluid ounces) of a standard commercially available nasal lavage solution. The patient received the lavage in the supine position with head tilted back, allowing the rhCC10 formulation to settle in the sinuses for 3-5 minutes. The patient then sat up, allowing the lavage to flow out and be expelled by nose blowing. The lavage was administered twice per day for 2 days, then once per day for 3 days, then discontinued. A CT scan performed 21 days after the initial dose of rhCC10 revealed complete resolution of the sinus infection without evidence of scarring, epithelial thickening, or other remaining blockage. The rhCC10 formulation mediated a potent anti-inflammatory response, which was caused by a bacterial infection and not allergy. rhCC10 further mediated an anti-inflammatory response when standard anti-inflammatory therapy in the form of intranasal corticosteroids failed. rhCC10 also facilitated clearance of the bacterial infection, which resolved without the use of additional antibiotics. Finally, rhCC10 mediated a complete recovery of the nasal epithelia, avoiding the scarring, fibrosis, and epithelial thickening that typically accompanies such severe infections.

EXAMPLE 8

Intranasal Formulation of rhCC10

Intranasal delivery of rhCC10 is useful for example, when treating upper respiratory (nasal and sinus and upper airway) inflammation and fibrosis, due to perennial allergy, infection, or some other form of acute or chronic upper respiratory irritation. rhCC10 is soluble in a wide range of aqueous solutions, over a wide range of pH values, for example 3.9-8.5, and in a wide range of salt concentrations (for example 0.1%-4%), as well as a variety of alcohol/water mixtures (for example 0.1%-90% ethanol). Thus, rhCC10 has the solubility and stability characteristics, to be used with a wide range of intranasal dispensing devices, including, but not limited to, for example, simple squirt bottles with uncontrolled volumetric doses for self-administration of liquid aerosols, pump-action or pressurized canister metered dose devices for self-administration of liquid aerosols, propellant-driven dry powder or liquid aerosol metered dose devices for self-administration, gel-laden nasal swabs for topical delivery to the nasal passages, and drug-loaded syringes for deeper topical administration and sinus lavage, for voluntary or involuntary administration to the conscious or unconscious patient.

\* \* \*

Based on the foregoing, the critical ranges for rhCC10 dosages effective to safely treat, cure and prevent nasal rhinitis, especially non-allergic rhinitis, nasal sinusitis, chronic rhinosinusitis, and nasal polyposis have been found. Accordingly, the present invention provides a safe and well-tolerated intranasal rhCC10 based therapy effective at treating the symptoms of nasal rhinitis, especially non-allergic rhinitis, nasal sinusitis, chronic rhinosinusitis, and nasal polyposis thus reducing the significant morbidities in child and adult patients suffering from these conditions, while not causing any dangerous side effects.

The invention claimed is:

1. A method of treating rhinosinusitis caused by infection in the nasal passages of a patient comprising: administering recombinant human Clara Cell 10 kDa protein ("rhCC10") at a concentration no greater than 2 milligrams/milliliter onto an intranasal mucosal membrane of a patient.

2. The method of claim 1 wherein the amount of rhCC10 administered is between 1.5 micrograms and 1.5 milligrams per day.

3. The method of claim 1 wherein the amount of rhCC10 administered is less than 1.1 milligrams per day.

4. The method of claim 1 wherein the amount of rhCC10 administered is 0.75 micrograms to 650 micrograms per day.

5. The method of claim 1, wherein the amount of rhCC10 administered is 0.5 micrograms to 370 micrograms per day.

6. The method of claim 1 wherein the rhCC10 is administered three times per day.

7. The method of claim 1 wherein the rhCC10 is administered two times per day.

8. The method of claim 1 wherein the rhCC10 is administered to the nasal passages by instillation, lavage, swab applicator, or spray.

9. The method of claim 1 wherein the rhCC10 is administered in combination with an antibiotic, an anti-histamine, a decongestant, a mucolytic, an analgesic, a local-acting vasoconstrictor, a leukotriene receptor antagonist, a steroid, a nasal excipient, or any combination thereof.

10. The method of claim 1, wherein the rhCC10 is administered at a concentration of 250 micrograms per milliliter in 0.65% sodium chloride, disodium phosphate, phenylcarbinol, monosodium phosphate, and benzalkonium chloride at a pH of 4.0-8.0.

11. The method of claim 1 wherein rhCC10 is administered in the pharmaceutical composition in a dosage of 20-50 micrograms per nostril up to four times per day.

12. A method of slowing growth or regrowth of nasal polyps caused by infection in a patient comprising: administering rhCC10 at a concentration no greater than 2 milligrams/milliliter onto an intranasal mucosal membrane of a patient.

13. The method of claim 12 wherein the amount of rhCC10 administered is between 1.5 micrograms and 1.5 milligrams per day.

14. The method of claim 12 wherein the amount of rhCC10 administered is less than 1.1 milligrams per day.

15. The method of claim 12 wherein the amount of rhCC10 administered is 0.75 micrograms to 650 micrograms per day.

16. The method of claim 12 wherein the amount of rhCC10 administered is 0.5 micrograms to 370 micrograms per day.

17. The method of claim 12 wherein the rhCC10 is administered three times per day.

18. The method of claim 12 wherein the rhCC10 is administered two times per day.

19. The method of claim 12 wherein the rhCC10 is administered to the nasal passages by instillation, lavage, swab applicator, or spray.

20. The method of claim 12 wherein the rhCC10 is administered in combination with an antibiotic, an anti-histamine, a decongestant, a mucolytic, an analgesic, a local-acting vasoconstrictor, a leukotriene receptor antagonist, a steroid, a nasal excipient, or any combination thereof.

21. The method of claim 12, wherein the rhCC10 is administered at a concentration of 250 micrograms per milliliter in 0.65% sodium chloride, disodium phosphate, phenylcarbinol, monosodium phosphate, and benzalkonium chloride at a pH of 4.0-8.0.

22. The method of claim 12 wherein rhCC10 is administered in the pharmaceutical composition in a dosage of 20-50 micrograms per nostril up to four times per day.

23. A method of treating chronic or recurrent bacterial sinus infection in a patient comprising: administering rhCC10 at a concentration no greater than 2 milligrams/milliliter onto an intranasal mucosal membrane of a patient.

24. The method of claim 23 wherein the amount of rhCC10 administered is between 1.5 micrograms and 1.5 milligrams per day.

25. The method of claim 23 wherein the amount of rhCC10 administered is less than 1.1 milligrams per day.

26. The method of claim 23 wherein the amount of rhCC10 administered is 0.75 micrograms to 650 micrograms per day.

27. The method of claim 23 wherein the amount of rhCC10 administered is 0.5 micrograms to 370 micrograms per day.

28. The method of claim 23 wherein the rhCC10 is administered three times per day.

29. The method of claim 23 wherein the rhCC10 is administered two times per day.

30. The method of claim 23 wherein the rhCC10 is administered to the nasal passages by instillation, lavage, swab applicator, or spray.

31. The method of claim 23 wherein the rhCC10 is administered in combination with an antibiotic, an anti-histamine, a decongestant, a mucolytic, an analgesic, a local-acting vasoconstrictor, a leukotriene receptor antagonist, a steroid, a nasal excipient, or any combination thereof.

32. The method of claim 23, wherein the rhCC10 is administered at a concentration of 250 micrograms per milliliter in 0.65% sodium chloride, disodium phosphate, phenylcarbinol, monosodium phosphate, and benzalkonium chloride at a pH of 4.0-8.0.

33. The method of claim 23 wherein rhCC10 is administered in the pharmaceutical composition in a dosage of 20-50 micrograms per nostril up to four times per day.

34. A method of treating sinus pain caused by infection in a patient comprising: administering rhCC10 at a concentration no greater than 2 milligrams/milliliter onto an intranasal mucosal membrane of a patient.

35. The method of claim 34 wherein the amount of rhCC10 administered is between 1.5 micrograms and 1.5 milligrams per day.

36. The method of claim 34 wherein the amount of rhCC10 administered is less than 1.1 milligrams per day.

37. The method of claim 34 wherein the amount of rhCC10 administered is 0.75 micrograms to 650 micrograms per day.

38. The method of claim 34 wherein the amount of rhCC10 administered is 0.5 micrograms to 370 micrograms per day.

39. The method of claim 34 wherein the rhCC10 is administered three times per day.

40. The method of claim 34 wherein the rhCC10 is administered two times per day.

41. The method of claim 34 wherein the rhCC10 is administered to the nasal passages by instillation, lavage, swab applicator, or spray.

42. The method of claim 34 wherein the rhCC10 is administered in combination with an antibiotic, an antihistamine, a decongestant, a mucolytic, an analgesic, a local-acting vasoconstrictor, a leukotriene receptor antagonist, a steroid, a nasal excipient, or any combination thereof.

43. The method of claim 34, wherein the: rhCC10 is administered at a concentration of 250 micrograms per milliliter in 0.65% sodium chloride, disodium phosphate, phenylcarbinol, monosodium phosphate, and benzalkonium chloride at a pH of 4.0-8.0.

44. The method of claim 34 wherein rhCC10 is administered in the pharmaceutical composition in a dosage of 20-50 micrograms per nostril up to four times per day.

45. A method of: treating rhinosinusitis caused by infection, slowing growth or regrowth of nasal polyps caused by infection, treating chronic or recurrent bacterial sinus infection, or treating sinus pain caused by infection in a patient comprising administering rhCC10 via a squeeze spray bottle, pump action spray device, metered dose nasal actuator, syringe-type instillation device, nasal swab applicator, or "Neti pot" lavage to the surfaces of the nasal passages.

* * * * *